(12) United States Patent
Galvin et al.

(10) Patent No.: US 6,586,175 B1
(45) Date of Patent: Jul. 1, 2003

(54) GENOTYPING THE HUMAN UDP-GLUCURONOSYLTRANSFERASE 2B7 (UGT2B7) GENE

(75) Inventors: Margaret Galvin, San Diego, CA (US); Andrew Miller, San Mateo, CA (US); Laura Penny, San Diego, CA (US); Michael Riedy, San Diego, CA (US)

(73) Assignee: DNA Sciences Laboratories, Inc., Morrisville, NC (US)

( * ) Notice: Subject to any disclaimer, the term of this patent is extended or adjusted under 35 U.S.C. 154(b) by 0 days.

(21) Appl. No.: 09/356,806

(22) Filed: Jul. 20, 1999

Related U.S. Application Data

(60) Provisional application No. 60/094,391, filed on Jul. 28, 1998.

(51) Int. Cl.$^7$ .......................... C07H 21/04; C12Q 1/68
(52) U.S. Cl. .................. 435/6; 536/23.1; 536/24.31; 435/91.2
(58) Field of Search .............................. 536/23.1, 24.31; 435/6, 91.2

(56) References Cited

U.S. PATENT DOCUMENTS 5,641,668 A  6/1997 Berger et al. ................ 435/193

FOREIGN PATENT DOCUMENTS

WO   WO 92 12987   8/1992

OTHER PUBLICATIONS

Radominska–Pandya et al. "UDP–glucuronosyltransferases in human intestinal mucosa" Biochemica et Biophysica Acta, vol. 1394, pp. 199–208, 1998.*
Jin et al. "Complimentary deoxyribonuclei acid cloning and expression of a human liver uridine diphosphate–glucuronosyltransferase glucuronidating carboxylic acid–containing drugs" J. Pharm. and Exper. Therapeutics, vol. 264, No. 1, pp. 475–479, 1993.*
Strassburg et al. "Regulation and function of family 1 and family 2 UGT1A and UGST2b in human oesophagus" J.Biochem. vol. 338, pp. 489–498, 1999.*
GenBank Attachments #2.*
Genbank Attachment of J05428, U91582, H66231, T62130, H70730.*
Belanger et al "Expression of transcripts encoding steroid UDP–glucuronosyltransferases in human prostate hyperplastic tissue and the LNCaP cell line" Molecular and Cellular Endocrinology, vol. 113, p. 165–173, 1995.*
Beaulieu et al., *J. Biol. Chem.*, 271(37):22855–22862 (1996).
Burchell, Entrez Accession No. Y00317 (1987).
Burchell et al., *Life Sciences*, 57(20):1819–1831 (1995).
Ciotti et al., *Pharmacogenetics*, 7(7):485–495 (1997).
Coffman et al., *Drug Metabolism and Disposition*, 25(1):1–4 (1997).
Cohen et al., *Eur. J. Biochem.*, 242(3):550–556 (1996).
De Wildt et al., *Clin. Pharmacokinetics*, 36(6):439–452 (1999).
Green et al., *Drug Metabolism and Disposition*, 22(5):799–805 (1994).
Jin et al., *Biochem. Biophys. Res. Commun.*, 194(1):496–503 (1993).
Levesque et al., *Pharmacogenetics*, 7(4):317–325 (1997).
Levesque et al., *Pharmacogenetics*, 9(2):207–216 (1999).
Mackenzie et al., *Pharmacogenetics*, 7(4):255–269 (1997).
MacLeod et al., Proc. American Association for Cancer Research Annual Meeting, 40:243–244 (1999).
Monaghan et al., *Genomics*, 23(2):496–499 (1994).
Monaghan et al., *Genomics*, 13(3):908–909 (1992).
Radominska et al., *Biochim. Biphys. Acta*, 1205(1):75–82 (1994).
Ritter et al., *J. Biol. Chemistry*, 265(14):7900–7906 (1990).
Ritter et al., *J. Biol. Chemistry*, 266(2):1043–1047 (1991).

\* cited by examiner

Primary Examiner—W. Gary Jones
Assistant Examiner—Jeanine Goldberg
(74) Attorney, Agent, or Firm—Sheridan Ross P.C.

(57) ABSTRACT

Genetic polymorphisms are identified in the human UGT2B4, UGT2B7 and UGT2B15 genes that alter UGT2B activity. Nucleic acids comprising the polymorphic sequences are used to screen patients for altered metabolism for UGT2B substrates, potential drug-drug interactions, and adverse/side effects, as well as diseases that result from environmental or occupational exposure to toxins. The nucleic acids are used to establish animal, cell and in vitro models for drug metabolism.

7 Claims, No Drawings

SEQUENCE LISTING

<160> NUMBER OF SEQ ID NOS: 164

<210> SEQ ID NO 1
<211> LENGTH: 1323
<212> TYPE: DNA
<213> ORGANISM: H. sapiens
<220> FEATURE:
<221> NAME/KEY: Other
<222> LOCATION: (140)...(897)

<400> SEQUENCE: 1

```
tcatctacct tttagttgtc tctttgtcat ccacatgctc agactgttaa tataatgtat      60
ttactttgaa gtgtaaaagt tacattttaa cttcttgact gatttatact ggatgtcacc     120
atgagaaatg acagaaagga gcagcaactg gaaaacaagc attgcattgc atcaggatgt     180
ctatgaaatg gacttcagct cttctgctga tacagctgag ctgttacttt agctctggga     240
gttgtggaaa ggtgctggtg tggcccacag aattcagcca ctggatgaat ataaagacaa     300
tcctggatga acttgtccag agaggtcatg aggtgactgt attggcatct tcagcttcca     360
tttctttcga tcccaacagc ccatctactc ttaaatttga agtttatcct gtatctttaa     420
ctaaaactga gtttgaggat attatcaagc agctggttaa gagatgggca gaacttccaa     480
```

-continued

| | |
|---|---|
| aagacacatt ttggtcatat ttttcacaag tacaagaaat catgtggaca tttaatgaca | 540 |
| tacttagaaa gttctgtaag gatatagttt caaataagaa acttatgaag aaactacagg | 600 |
| agtcaagatt tgatgttgtt cttgcagatg ctgttttccc ctttggtgag ctgctggccg | 660 |
| agttacttaa ataccctttt gtctacagcc tccgcttctc tcctggctac gcaattgaaa | 720 |
| agcatagtgg aggacttctg ttccctcctt cctatgtgcc tgttgttatg tcagaactaa | 780 |
| gtgaccaaat gactttcata gagagggtaa aaaatatgat ctatgtgctt tatttttgaat | 840 |
| tttggttcca aatatttgac atgaagaagt gggatcagtt ctacagtgaa gttctaggta | 900 |
| agtaacttttt ttgattggta acatgaagat ctaactttct tgtacctttg aagctgagtt | 960 |
| tgtataaagc cataaagtca gggtagtggg gtatttttgt aatgaattta tcaaatgaaa | 1020 |
| ttgtaagatg atctaccaaa ctcacaagca ctatagaaaa tgtaaattat aggatcagtt | 1080 |
| aaaactctgt ggccatcact catacagaag actccaggaa gtcataagcc tgtatattag | 1140 |
| tgcacctaag atttctttaa gcaatcacat atctgtttta ttatacatttt tttcatctta | 1200 |
| aaaaaaagtc agacttattc agaaacatct tgctgaatgc atactggtag attgagtagt | 1260 |
| tacacattttt ttagaactat ctatataaca ttgcagaaat tgtttttttct tgtatatttg | 1320 |
| cag | 1323 |

<210> SEQ ID NO 2
<211> LENGTH: 746
<212> TYPE: DNA
<213> ORGANISM: H. sapiens
<220> FEATURE:
<221> NAME/KEY: Other
<222> LOCATION: (195)...(344)

<400> SEQUENCE: 2

| | |
|---|---|
| ttcttgtaaa tacacatggg taaaatatat aatacataaa aattaaatta tgcctatata | 60 |
| cgaatatatg tatttttttt caaggcacaa acactttgcc tacattttttg cccacattat | 120 |
| tctaacttct ttcagaaaat tacctagttt aattatcttg tgtcatctat cttttctttt | 180 |
| ttttccccc atcaggaaga cccactacgt tatctgagac aatggcaaaa gctgacatat | 240 |
| ggcttattcg aaactactgg gatttttcaat ttcctcaccc actcttacca aatgttgagt | 300 |
| tcgttggagg actccactgc aaacctgcca aaccccctacc gaaggtaaac tattactgtt | 360 |
| tgttttgtct gctttgaagt ttcagtacga atggttctat attcattcaa agtgtttgac | 420 |
| ttacactgga agaaaggtgg aagtgggaag agtaaagcag ataccaatta gaaactgacg | 480 |
| tacatgttga tactatcaca agtttatgaa tttcatcatt attaccaata agagggata | 540 |
| ctaaagagac tttgaaaata gggttggtaa attaaagctt tgattatgca acatataaga | 600 |
| aggtactggc cattcattca aagaatattt ataaagagat tagcacacac cacaggtacg | 660 |
| tgtatgggac acagtttcta tcccaacaca ccttacattc tattttgaaa gatagaatat | 720 |
| atgcaagtaa taaaaactgt gtaaaa | 746 |

<210> SEQ ID NO 3
<211> LENGTH: 785
<212> TYPE: DNA
<213> ORGANISM: H. sapiens
<220> FEATURE:
<221> NAME/KEY: Other
<222> LOCATION: (238)...(369)

<400> SEQUENCE: 3

| | |
|---|---|
| ttcacaaacg cacacacata cacacacaca tatttacaca aagacccttta acagaggcaa | 60 |

-continued

```
cctatctcat attatacata ttgcaaaaaa aactgagtaa ttgagtcagt taaaaaacat        120
cctttactcc aataattcct gataaaactt gattttctct cttttttataa caattctttc       180 acagtgcttg ctgtgctgat aatctattat gatagaacaa attctttttt ttcacaggaa        240
atggaagagt ttgtccagag ctctggagaa atggtgttg tggtgttttc tctggggtcg         300
atggtcagta acacgtcaga agaaagggcc aatgtaattg catcagccct tgccaagatc        360
ccacaaaagg taagataaaa tgttttaatg gtgtaaaaaa ctactgaaag aggctgttaa        420
agtttgtaaa gaacccaatt gtagaaactt cctgcctata tattcagctg ttgggaaagc       480
actaattatc tcagatatta attcaaaatc aaaaatatgt atggaagatg ataaactcat        540
acagaaggtg ttttttcattg gtaattaatt tggcattaat attgtgatca ggaataaata      600
caattaagag ttgcaggtaa agttttggta ttatcatgat actggggtca ggtaagagct       660
atcaccaaat tctgccctg tgatttgatc cttttgttta agaactcctg agggcgatgt        720
acatcctaca ggtgttagaa aacgttacat tttaatgagt aacttcacta gcacaataac       780
aatag                                                                    785
```

<210> SEQ ID NO 4
<211> LENGTH: 1138
<212> TYPE: DNA
<213> ORGANISM: H. sapiens
<220> FEATURE:
<221> NAME/KEY: Other
<222> LOCATION: (395)...(482)

<400> SEQUENCE: 4

```
catctgttat tttttgagtt tttaataatg gccattctga ctggtgtgag atggtatctc        60
tttgtggatt taaccagtga tgtaaacctt ttttttcatat agtggtttgc cacatatagt     120
tttcttttga aaagtgtaac aacttttttaa atacttgaac ttttcattga ttatcttatt      180
tgtctaagct actattttga aaaatcatga tttccttata tacctaatta tgaaattaag       240
gaaatgaaat atgagtattc tatttacatc agtctgagta gttcttgtta cttaacatcc       300
cttgttcttc tcattgttaa tctctttaga tttctaacat tctatgactt tgagttcca       360 ctcatggaat aagatatttt cttcactgta acaggttctg tggagatttg atgggaataa      420
accagatact ttaggactca atactcggct gtacaagtgg ataccccaga atgatcttct     480
tggtaagtct ctgaagaaca aatactgaat atattagtaa cagattatta aagtgttaat      540
agctatcatg aaacaagctt actgaacatt tgttatggaa aaacttaaaa ataaaatgaa      600
acttctttat atttattttc cagtcccggg ggaaaagaat aaattgttgg cattttatga     660
tatgcaccca cattctttac aatcagagtc agtatctt tatttcaggt gttattacct       720
cccacagaat ttttctggca cttcctgggt tgtcttcctt tctcatattt ctacaacttt      780
acacctgttc tttcctcctc tgtagggtta tttcaaatgt cactaaaagt aacagctctt      840
ctgctatcac cagggatgct gcattttctg taggattaaa tccctaatct taatcaaaaa      900
gtgatgacac atttcataat gaaatgtgac ctgtctttcc tcaattctag caccaccacc      960
acctcactgc ctgctgcctt gcacacccta catatccaac tccgtgactg tacttaagag     1020
aacacattct ggctgggcac ggtgctcacg cctgcaatcc tagcactttg ggaggctgat    1080
ggcaggtgga ttgactgagc tcaggagttc aagaccatcc tgggcaacat ggtgaaac      1138
```

<210> SEQ ID NO 5
<211> LENGTH: 689

```
<212> TYPE: DNA
<213> ORGANISM: H. sapiens
<220> FEATURE:
<221> NAME/KEY: Other
<222> LOCATION: (123)...(342)

<400> SEQUENCE: 5
aaaaacaatt ttaattcagt tcagtgtgtt atctaggaaa caccgtcaca ttcagattct      60
tccattgtgc atttctcatt ttattcctat gaataatttt gctaaaattc atccaatcct     120
aggtcaccca aaaccagag cttttataac tcatggtgga gccaatggca tctatgaggc     180
aatctaccat ggaatcccta tggtgggcgt tccattgttt gcagatcaac ctgataacat     240
tgcacacatg aaggccaagg gagcagctgt tagtttggac ttccacacaa tgtcgagtac     300
agacttactc aatgcactga agacagtaat taatgatcct ttgtgagtat aacttttttt     360
ttactcggtg gtctttatag ataggttccc ttgtgaatag tgagtatgac ttttatcctt     420
tttataagcg actgatttcg aaagaattta agtgatttaa acaatctgaa atctgctttt     480
atttttgagt ggttatttaa aaattttatt tgaaccacat acatttaatg aataatcaat     540
tattgaaata attttctaca caaaataat tttaaagtga tatagataag aagacatttt     600
aaaataaatt tgacgtaatc aatccacagt agaaaggaaa gataaacttg acgtaatata     660
ataaaatatt ttaattcaat atctaaaat                                       689

<210> SEQ ID NO 6
<211> LENGTH: 1589
<212> TYPE: DNA
<213> ORGANISM: H. sapiens
<220> FEATURE:
<221> NAME/KEY: Other
<222> LOCATION: (731)...(1475)

<400> SEQUENCE: 6
atgcttaagc aatgggtagc ctttcttcat gatgtgatta tttcacactg cagcctgtat      60
caaaacatct catgcacctc atagaaaaat acccctacta tgtaaccaca aaaactaaaa     120
attaaaagaa aataaaattg ctcatatgtt ctctgcctca ataattaac tttctcacct     180
gaccctccat ttttacttta aaatatttg tcaattatga aattccaatt taaaagccaa     240
actttctatg atgactcaaa ttaaaataca cacattctat gtcaattcta tgacatttac     300
tttgaatgat ctggcacttt aaaaaccttt cgtggacttg atgtgctcag gcaaattaac     360
ttaccttctc ttttttttgag agggaagtct cactctgtca ccaggctgga gtgcagtggt     420
gtgattgtgg ctcactgcaa cttccgcctc ttgggttcaa gcgattctcc tgcctcagcc     480
tctcaagtag ctgggactac aggcacatgc caccacgcct gggtaatctt tttttttttt     540
ttttttttca tattttact ggagacgggg tgaacgggt ttcaccgtgt tagccaggat     600
ggtcttgatc tcctgacctc gtgatccgcc cgcctcgacc tcgaaagtg ctgggattgc     660
aggtgtgagc ctccgtgcct ggccaaattg acttactttc aatgttgata cttttctgct     720
tatcgtttag atataaagag aatgctatga aattatcaag aattcatcat gatcaaccag     780
tgaagcccct tgatcgagca gtcttctgga ttgaatttgt catgcgccat aaaggagcca     840
agcaccttcg ggttgcagcc cacgacctca cctggttcca gtaccactct ttggatgtga     900
ctgggttcct gctggcctgt gtggcaactg tgatattcat catcacaaaa tgtctgtttt     960
gtgtctggaa gtttgttaga acaggaaaga aggggaaaag agattaatta cgtctgaggc    1020
tggaagctgg gaaacccaat aaatgaactc ctttagttta ttacaacaag aagacgttgt    1080
```

-continued

```
gatacaagag attcctttct tcttgtgaca aaacatcttt caaaacttac cttgtcaagt      1140
caaaatttgt tttagtacct gtttaaccat tagaaatatt tcatgtcaag gaggaaaaca      1200
ttagggaaaa caaaaatgat ataaagccat acgaggttat attgaaatgt attgagctta      1260
tattgaaatt tattgttcca attcacaggt tacatgaaaa aaaatttact aagcttaact      1320
acatgtcaca cattgtacat ggaaacaaga acattaagaa gtccactgac agtatcagta      1380
ctgttttgca atactcagc atactttgga tccatttcat gcaggattgt gttgttttaa       1440
ctgttgttga ggaaactaat aaataattaa attgtataga aagtctcttc ctcttgatat      1500
tttgagatga ttagtgctgc ttggctttta ttgtgcatcg tgcttcaacg tcattttttt      1560
tcctaaaagg tatgataaaa aatgcttac                                        1589
```

<210> SEQ ID NO 7
<211> LENGTH: 2092
<212> TYPE: DNA
<213> ORGANISM: H. sapiens
<220> FEATURE:
<221> NAME/KEY: CDS
<222> LOCATION: (38)...(1621)

<400> SEQUENCE: 7

```
agcagcaact ggaaaacaag cattgcattg catcagg atg tct atg aaa tgg act       55
                                        Met Ser Met Lys Trp Thr
                                          1               5 tca gct ctt ctg ctg ata cag ctg agc tgt tac ttt agc tct ggg agt       103
Ser Ala Leu Leu Leu Ile Gln Leu Ser Cys Tyr Phe Ser Ser Gly Ser
             10                  15                  20 tgt gga aag gtg ctg gtg tgg ccc aca gaa ttc agc cac tgg atg aat       151
Cys Gly Lys Val Leu Val Trp Pro Thr Glu Phe Ser His Trp Met Asn
         25                  30                  35 ata aag aca atc ctg gat gaa ctt gtc cag aga ggt cat gag gtg act       199
Ile Lys Thr Ile Leu Asp Glu Leu Val Gln Arg Gly His Glu Val Thr
     40                  45                  50 gta ttg gca tct tca gct tcc att tct ttc gat ccc aac agc cca tct       247
Val Leu Ala Ser Ser Ala Ser Ile Ser Phe Asp Pro Asn Ser Pro Ser
 55                  60                  65                  70 act ctt aaa ttt gaa gtt tat cct gta tct tta act aaa act gag ttt       295
Thr Leu Lys Phe Glu Val Tyr Pro Val Ser Leu Thr Lys Thr Glu Phe
                 75                  80                  85 gag gat att atc aag cag ctg gtt aag aga tgg gca gaa ctt cca aaa       343
Glu Asp Ile Ile Lys Gln Leu Val Lys Arg Trp Ala Glu Leu Pro Lys
             90                  95                 100 gac aca ttt tgg tca tat ttt tca caa gta caa gaa atc atg tgg aca       391
Asp Thr Phe Trp Ser Tyr Phe Ser Gln Val Gln Glu Ile Met Trp Thr
        105                 110                 115 ttt aat gac ata ctt aga aag ttc tgt aag gat ata gtt tca aat aag       439
Phe Asn Asp Ile Leu Arg Lys Phe Cys Lys Asp Ile Val Ser Asn Lys
    120                 125                 130 aaa ctt atg aag aaa cta cag gag tca aga ttt gat gtt gtt ctt gca       487
Lys Leu Met Lys Lys Leu Gln Glu Ser Arg Phe Asp Val Val Leu Ala
135                 140                 145                 150 gat gct gtt ttc ccc ttt ggt gag ctg ctg gcc gag tta ctt aaa ata       535
Asp Ala Val Phe Pro Phe Gly Glu Leu Leu Ala Glu Leu Leu Lys Ile
                155                 160                 165 ccc ttt gtc tac agc ctc cgc ttc tct cct ggc tac gca att gaa aag       583
Pro Phe Val Tyr Ser Leu Arg Phe Ser Pro Gly Tyr Ala Ile Glu Lys
            170                 175                 180 cat agt gga gga ctt ctg ttc cct cct tcc tat gtg cct gtt gtt atg       631
His Ser Gly Gly Leu Leu Phe Pro Pro Ser Tyr Val Pro Val Val Met
```

|  |  |  |  |  |  |  |  |  |  |  |  |  |  |  |  |
|---|---|---|---|---|---|---|---|---|---|---|---|---|---|---|---|
|  | 185 |  |  |  | 190 |  |  |  |  | 195 |  |  |  |  |  |

```
tca gaa cta agt gac caa atg act ttc ata gag agg gta aaa aat atg      679
Ser Glu Leu Ser Asp Gln Met Thr Phe Ile Glu Arg Val Lys Asn Met
    200             205                 210 atc tat gtg ctt tat ttt gaa ttt tgg ttc caa ata ttt gac atg aag      727
Ile Tyr Val Leu Tyr Phe Glu Phe Trp Phe Gln Ile Phe Asp Met Lys
215             220                 225                 230 aag tgg gat cag ttc tac agt gaa gtt cta gga aga ccc act acg tta      775
Lys Trp Asp Gln Phe Tyr Ser Glu Val Leu Gly Arg Pro Thr Thr Leu
                235                 240                 245 tct gag aca atg gca aaa gct gac ata tgg ctt att cga aac tac tgg      823
Ser Glu Thr Met Ala Lys Ala Asp Ile Trp Leu Ile Arg Asn Tyr Trp
            250                 255                 260 gat ttt caa ttt cct cac cca ctc tta cca aat gtt gag ttc gtt gga      871
Asp Phe Gln Phe Pro His Pro Leu Leu Pro Asn Val Glu Phe Val Gly
        265                 270                 275 gga ctc cac tgc aaa cct gcc aaa ccc cta ccg aag gaa atg gaa gag      919
Gly Leu His Cys Lys Pro Ala Lys Pro Leu Pro Lys Glu Met Glu Glu
    280                 285                 290 ttt gtc cag agc tct gga gaa aat ggt gtt gtg gtg ttt tct ctg ggg      967
Phe Val Gln Ser Ser Gly Glu Asn Gly Val Val Val Phe Ser Leu Gly
295             300                 305                 310 tcg atg gtc agt aac acg tca gaa gaa agg gcc aat gta att gca tca     1015
Ser Met Val Ser Asn Thr Ser Glu Glu Arg Ala Asn Val Ile Ala Ser
                315                 320                 325 gcc ctt gcc aag atc cca caa aag gtt ctg tgg aga ttt gat ggg aat     1063
Ala Leu Ala Lys Ile Pro Gln Lys Val Leu Trp Arg Phe Asp Gly Asn
            330                 335                 340 aaa cca gat act tta gga ctc aat act cgg ctg tac aag tgg ata ccc     1111
Lys Pro Asp Thr Leu Gly Leu Asn Thr Arg Leu Tyr Lys Trp Ile Pro
        345                 350                 355 cag aat gat ctt ctt ggt cac cca aaa acc aga gct ttt ata act cat     1159
Gln Asn Asp Leu Leu Gly His Pro Lys Thr Arg Ala Phe Ile Thr His
    360                 365                 370 ggt gga gcc aat ggc atc tat gag gca atc tac cat gga atc cct atg     1207
Gly Gly Ala Asn Gly Ile Tyr Glu Ala Ile Tyr His Gly Ile Pro Met
375             380                 385                 390 gtg ggc gtt cca ttg ttt gca gat caa cct gat aac att gca cac atg     1255
Val Gly Val Pro Leu Phe Ala Asp Gln Pro Asp Asn Ile Ala His Met
                395                 400                 405 aag gcc aag gga gca gct gtt agt ttg gac ttc cac aca atg tcg agt     1303
Lys Ala Lys Gly Ala Ala Val Ser Leu Asp Phe His Thr Met Ser Ser
            410                 415                 420 aca gac tta ctc aat gca ctg aag aca gta att aat gat cct tta tat     1351
Thr Asp Leu Leu Asn Ala Leu Lys Thr Val Ile Asn Asp Pro Leu Tyr
        425                 430                 435 aaa gag aat gct atg aaa tta tca aga att cat cat gat caa cca gtg     1399
Lys Glu Asn Ala Met Lys Leu Ser Arg Ile His His Asp Gln Pro Val
    440                 445                 450 aag ccc ctt gat cga gca gtc ttc tgg att gaa ttt gtc atg cgc cat     1447
Lys Pro Leu Asp Arg Ala Val Phe Trp Ile Glu Phe Val Met Arg His
455                 460                 465                 470 aaa gga gcc aag cac ctt cgg gtt gca gcc cac gac ctc acc tgg ttc     1495
Lys Gly Ala Lys His Leu Arg Val Ala Ala His Asp Leu Thr Trp Phe
                475                 480                 485 cag tac cac tct ttg gat gtg act ggg ttc ctg ctg gcc tgt gtg gca     1543
Gln Tyr His Ser Leu Asp Val Thr Gly Phe Leu Leu Ala Cys Val Ala
            490                 495                 500 act gtg ata ttc atc atc aca aaa tgt ctg ttt tgt gtc tgg aag ttt     1591
```

```
Thr Val Ile Phe Ile Ile Thr Lys Cys Leu Phe Cys Val Trp Lys Phe
        505                 510                 515 gtt aga aca gga aag aag ggg aaa aga gat taattacgtc tgaggctgga         1641
Val Arg Thr Gly Lys Lys Gly Lys Arg Asp
        520                 525 agctgggaaa cccaataaat gaactccttt agtttattac aacaagaaga cgttgtgata    1701
caagagattc ctttcttctt gtgacaaaac atctttcaaa acttaccttg tcaagtcaaa    1761
atttgtttta gtacctgttt aaccattaga aatatttcat gtcaaggagg aaaacattag    1821
ggaaaacaaa aatgatataa agccatacga ggttatattg aaatgtattg agcttatatt    1881
gaaatttatt gttccaattc acaggttaca tgaaaaaaaa tttactaagc ttaactacat    1941
gtcacacatt gtacatggaa acaagaacat taagaagtcc actgacagta tcagtactgt    2001
tttgcaaata ctcagcatac tttggatcca tttcatgcag gattgtgttg ttttaactgt    2061
tgttgaggaa actaataaat aattaaattg t                                    2092

<210> SEQ ID NO 8
<211> LENGTH: 528
<212> TYPE: PRT
<213> ORGANISM: H. sapiens

<400> SEQUENCE: 8

Met Ser Met Lys Trp Thr Ser Ala Leu Leu Leu Ile Gln Leu Ser Cys
1               5                   10                  15

Tyr Phe Ser Ser Gly Ser Cys Gly Lys Val Leu Val Trp Pro Thr Glu
            20                  25                  30

Phe Ser His Trp Met Asn Ile Lys Thr Ile Leu Asp Glu Leu Val Gln
        35                  40                  45

Arg Gly His Glu Val Thr Val Leu Ala Ser Ser Ala Ser Ile Ser Phe
    50                  55                  60

Asp Pro Asn Ser Pro Ser Thr Leu Lys Phe Glu Val Tyr Pro Val Ser
65                  70                  75                  80

Leu Thr Lys Thr Glu Phe Glu Asp Ile Ile Lys Gln Leu Val Lys Arg
                85                  90                  95

Trp Ala Glu Leu Pro Lys Asp Thr Phe Trp Ser Tyr Phe Ser Gln Val
            100                 105                 110

Gln Glu Ile Met Trp Thr Phe Asn Asp Ile Leu Arg Lys Phe Cys Lys
        115                 120                 125

Asp Ile Val Ser Asn Lys Lys Leu Met Lys Leu Gln Glu Ser Arg
    130                 135                 140

Phe Asp Val Val Leu Ala Asp Ala Val Phe Pro Phe Gly Glu Leu Leu
145                 150                 155                 160

Ala Glu Leu Leu Lys Ile Pro Phe Val Tyr Ser Leu Arg Phe Ser Pro
                165                 170                 175

Gly Tyr Ala Ile Glu Lys His Ser Gly Gly Leu Leu Phe Pro Pro Ser
            180                 185                 190

Tyr Val Pro Val Val Met Ser Glu Leu Ser Asp Gln Met Thr Phe Ile
        195                 200                 205

Glu Arg Val Lys Asn Met Ile Tyr Val Leu Tyr Phe Glu Phe Trp Phe
    210                 215                 220

Gln Ile Phe Asp Met Lys Lys Trp Asp Gln Phe Tyr Ser Glu Val Leu
225                 230                 235                 240

Gly Arg Pro Thr Thr Leu Ser Glu Thr Met Ala Lys Ala Asp Ile Trp
                245                 250                 255
```

```
Leu Ile Arg Asn Tyr Trp Asp Phe Gln Phe Pro His Pro Leu Leu Pro
            260                 265                 270

Asn Val Glu Phe Val Gly Gly Leu His Cys Lys Pro Ala Lys Pro Leu
            275                 280                 285

Pro Lys Glu Met Glu Glu Phe Val Gln Ser Ser Gly Glu Asn Gly Val
            290                 295                 300

Val Val Phe Ser Leu Gly Ser Met Val Ser Asn Thr Ser Glu Glu Arg
305                 310                 315                 320

Ala Asn Val Ile Ala Ser Ala Leu Ala Lys Ile Pro Gln Lys Val Leu
                325                 330                 335

Trp Arg Phe Asp Gly Asn Lys Pro Asp Thr Leu Gly Leu Asn Thr Arg
            340                 345                 350

Leu Tyr Lys Trp Ile Pro Gln Asn Asp Leu Leu Gly His Pro Lys Thr
            355                 360                 365

Arg Ala Phe Ile Thr His Gly Gly Ala Asn Gly Ile Tyr Glu Ala Ile
            370                 375                 380

Tyr His Gly Ile Pro Met Val Gly Val Pro Leu Phe Ala Asp Gln Pro
385                 390                 395                 400

Asp Asn Ile Ala His Met Lys Ala Lys Gly Ala Ala Val Ser Leu Asp
                405                 410                 415

Phe His Thr Met Ser Ser Thr Asp Leu Leu Asn Ala Leu Lys Thr Val
            420                 425                 430

Ile Asn Asp Pro Leu Tyr Lys Glu Asn Ala Met Lys Leu Ser Arg Ile
            435                 440                 445

His His Asp Gln Pro Val Lys Pro Leu Asp Arg Ala Val Phe Trp Ile
            450                 455                 460

Glu Phe Val Met Arg His Lys Gly Ala Lys His Leu Arg Val Ala Ala
465                 470                 475                 480

His Asp Leu Thr Trp Phe Gln Tyr His Ser Leu Asp Val Thr Gly Phe
            485                 490                 495

Leu Leu Ala Cys Val Ala Thr Val Ile Phe Ile Ile Thr Lys Cys Leu
            500                 505                 510

Phe Cys Val Trp Lys Phe Val Arg Thr Gly Lys Lys Gly Lys Arg Asp
            515                 520                 525

<210> SEQ ID NO 9
<211> LENGTH: 24
<212> TYPE: DNA
<213> ORGANISM: H. sapiens

<400> SEQUENCE: 9 tacctttag ttgtctcttt gtca                                    24

<210> SEQ ID NO 10
<211> LENGTH: 21
<212> TYPE: DNA
<213> ORGANISM: H. sapiens

<400> SEQUENCE: 10
ttcctggagt cttctgtatg a                                      21

<210> SEQ ID NO 11
<211> LENGTH: 20
<212> TYPE: DNA
<213> ORGANISM: H. sapiens

<400> SEQUENCE: 11
```

```
catcccttgt tcttctcatt                                                      20

<210> SEQ ID NO 12
<211> LENGTH: 20
<212> TYPE: DNA
<213> ORGANISM: H. sapiens

<400> SEQUENCE: 12
cgggactgga aaataaatat                                                      20

<210> SEQ ID NO 13
<211> LENGTH: 17
<212> TYPE: DNA
<213> ORGANISM: H. sapiens

<400> SEQUENCE: 13
ggggtttcac cgtgtta                                                         17

<210> SEQ ID NO 14
<211> LENGTH: 18
<212> TYPE: DNA
<213> ORGANISM: H. sapiens

<400> SEQUENCE: 14
aaagccaagc agcactaa                                                        18

<210> SEQ ID NO 15
<211> LENGTH: 20
<212> TYPE: DNA
<213> ORGANISM: H. sapiens

<400> SEQUENCE: 15
ccacatgctc agactgttaa                                                      20

<210> SEQ ID NO 16
<211> LENGTH: 19
<212> TYPE: DNA
<213> ORGANISM: H. sapiens

<400> SEQUENCE: 16
caaaaatacc ccactaccc                                                       19

<210> SEQ ID NO 17
<211> LENGTH: 21
<212> TYPE: DNA
<213> ORGANISM: H. sapiens

<400> SEQUENCE: 17
cccttgttct tctcattgtt a                                                    21

<210> SEQ ID NO 18
<211> LENGTH: 22
<212> TYPE: DNA
<213> ORGANISM: H. sapiens

<400> SEQUENCE: 18
ttcagtaagc ttgtttcatg at                                                   22

<210> SEQ ID NO 19
<211> LENGTH: 17
<212> TYPE: DNA
<213> ORGANISM: H. sapiens

<400> SEQUENCE: 19
```

```
cctggccaaa ttgactt                                                  17

<210> SEQ ID NO 20
<211> LENGTH: 18
<212> TYPE: DNA
<213> ORGANISM: H. sapiens

<400> SEQUENCE: 20
caggaaccca gtcacatc                                                 18

<210> SEQ ID NO 21
<211> LENGTH: 21
<212> TYPE: DNA
<213> ORGANISM: H. sapiens

<400> SEQUENCE: 21
ggggaaaaga gattaattac g                                             21

<210> SEQ ID NO 22
<211> LENGTH: 18
<212> TYPE: DNA
<213> ORGANISM: H. sapiens

<400> SEQUENCE: 22
agccaagcag cactaatc                                                 18

<210> SEQ ID NO 23
<211> LENGTH: 20
<212> TYPE: DNA
<213> ORGANISM: H. sapiens

<400> SEQUENCE: 23
tccaattcac aggttacatg                                               20

<210> SEQ ID NO 24
<211> LENGTH: 18
<212> TYPE: DNA
<213> ORGANISM: H. sapiens

<400> SEQUENCE: 24
agccaagcag cactaatc                                                 18

<210> SEQ ID NO 25
<211> LENGTH: 27
<212> TYPE: DNA
<213> ORGANISM: H. sapiens

<400> SEQUENCE: 25
tggatgaata taaagacaat cctggat                                       27

<210> SEQ ID NO 26
<211> LENGTH: 27
<212> TYPE: DNA
<213> ORGANISM: H. sapiens

<400> SEQUENCE: 26
tggatgaata taaacacaat cctggat                                       27

<210> SEQ ID NO 27
<211> LENGTH: 27
<212> TYPE: DNA
<213> ORGANISM: H. sapiens
```

-continued

<400> SEQUENCE: 27
aagtgttaat agttatcatg aaacaag                                              27

<210> SEQ ID NO 28
<211> LENGTH: 27
<212> TYPE: DNA
<213> ORGANISM: H. sapiens

<400> SEQUENCE: 28
aagtgttaat agctatcatg aaacaag                                              27

<210> SEQ ID NO 29
<211> LENGTH: 27
<212> TYPE: DNA
<213> ORGANISM: H. sapiens

<400> SEQUENCE: 29
tgaagcccct tgatcgagca gtcttct                                              27

<210> SEQ ID NO 30
<211> LENGTH: 27
<212> TYPE: DNA
<213> ORGANISM: H. sapiens

<400> SEQUENCE: 30
tgaagcccct tgaacgagca gtcttct                                              27

<210> SEQ ID NO 31
<211> LENGTH: 27
<212> TYPE: DNA
<213> ORGANISM: H. sapiens

<400> SEQUENCE: 31
tgaagcccct tgatcgagca gtcttct                                              27

<210> SEQ ID NO 32
<211> LENGTH: 27
<212> TYPE: DNA
<213> ORGANISM: H. sapiens

<400> SEQUENCE: 32
tgaagcccct tgatagagca gtcttct                                              27

<210> SEQ ID NO 33
<211> LENGTH: 27
<212> TYPE: DNA
<213> ORGANISM: H. sapiens

<400> SEQUENCE: 33
gatataaagc catacgaggt tatattg                                              27

<210> SEQ ID NO 34
<211> LENGTH: 27
<212> TYPE: DNA
<213> ORGANISM: H. sapiens

<400> SEQUENCE: 34
gatataaagc catatgaggt tatattg                                              27

<210> SEQ ID NO 35
<211> LENGTH: 26
<212> TYPE: DNA
<213> ORGANISM: H. sapiens

```
<400> SEQUENCE: 35
caggttacat gaaaaaaaat ttacta                                        26

<210> SEQ ID NO 36
<211> LENGTH: 26
<212> TYPE: DNA
<213> ORGANISM: H. sapiens

<400> SEQUENCE: 36
caggttacat gaaaaacaat ttacta                                        26

<210> SEQ ID NO 37
<211> LENGTH: 27
<212> TYPE: DNA
<213> ORGANISM: H. sapiens

<400> SEQUENCE: 37
ttgttgagga agctaataaa taattaa                                       27

<210> SEQ ID NO 38
<211> LENGTH: 27
<212> TYPE: DNA
<213> ORGANISM: H. sapiens

<400> SEQUENCE: 38
ttgttgagga aactaataaa taattaa                                       27

<210> SEQ ID NO 39
<211> LENGTH: 1854
<212> TYPE: DNA
<213> ORGANISM: H. sapiens
<220> FEATURE:
<221> NAME/KEY: CDS
<222> LOCATION: (15)...(1584)

<400> SEQUENCE: 39
```

| | | |
|---|---|---|
| tgcattgcac cagg atg tct gtg aaa tgg act tca gta att ttg cta ata<br>                  Met Ser Val Lys Trp Thr Ser Val Ile Leu Leu Ile<br>                   1                5                     10 | 50 |
| caa ctg agc ttt tgc ttt agc tct ggg aat tgt gga aag gtg ctg gtg<br>Gln Leu Ser Phe Cys Phe Ser Ser Gly Asn Cys Gly Lys Val Leu Val<br> 15                      20                    25 | 98 |
| tgg gca gca gaa tac agc cat tgg atg aat ata aag aca atc ctg gat<br>Trp Ala Ala Glu Tyr Ser His Trp Met Asn Ile Lys Thr Ile Leu Asp<br>    30                      35                    40 | 146 |
| gag ctt att cag aga ggt cat gag gtg act gta ctg gca tct tca gct<br>Glu Leu Ile Gln Arg Gly His Glu Val Thr Val Leu Ala Ser Ser Ala<br>45                  50                    55                    60 | 194 |
| tcc att ctt ttt gat ccc aac aac tcc tcc gct ctt aaa att gaa att<br>Ser Ile Leu Phe Asp Pro Asn Asn Ser Ser Ala Leu Lys Ile Glu Ile<br>             65                          70                       75 | 242 |
| tat ccc aca tct tta act aaa act gag ttg gag aat ttc atc atg caa<br>Tyr Pro Thr Ser Leu Thr Lys Thr Glu Leu Glu Asn Phe Ile Met Gln<br>        80                    85                    90 | 290 |
| cag att aag aga tgg tca gac ctt cca aaa gat aca ttt tgg tta tat<br>Gln Ile Lys Arg Trp Ser Asp Leu Pro Lys Asp Thr Phe Trp Leu Tyr<br>     95                    100                 105 | 338 |
| ttt tca caa gta cag gaa atc atg tca ata ttt ggt gac ata act aga<br>Phe Ser Gln Val Gln Glu Ile Met Ser Ile Phe Gly Asp Ile Thr Arg<br>110                 115                    120 | 386 |
| aag ttc tgt aaa gat gta gtt tca aat aag aaa ttt atg aaa aaa gta | 434 |

```
Lys Phe Cys Lys Asp Val Val Ser Asn Lys Lys Phe Met Lys Lys Val
125                 130                 135                 140 caa gag tca aga ttt gac gtc att ttt gca gat gct att ttt ccc tgt        482
Gln Glu Ser Arg Phe Asp Val Ile Phe Ala Asp Ala Ile Phe Pro Cys
                145                 150                 155 agt gag ctg ctg gct gag cta ttt aac ata ccc ttt gtg tac agt ctc        530
Ser Glu Leu Leu Ala Glu Leu Phe Asn Ile Pro Phe Val Tyr Ser Leu
            160                 165                 170 agc ttc tct cct ggc tac act ttt gaa aag cat agt gga gga ttt att        578
Ser Phe Ser Pro Gly Tyr Thr Phe Glu Lys His Ser Gly Gly Phe Ile
        175                 180                 185 ttc cct cct tcc tac gta cct gtt gtt atg tca gaa tta act gat caa        626
Phe Pro Pro Ser Tyr Val Pro Val Val Met Ser Glu Leu Thr Asp Gln
    190                 195                 200 atg act ttc atg gag agg gta aaa aat atg atc tat gtg ctt tac ttt        674
Met Thr Phe Met Glu Arg Val Lys Asn Met Ile Tyr Val Leu Tyr Phe
205                 210                 215                 220 gac ttt tgg ttc gaa ata ttt gac atg aag aag tgg gat cag ttt tat        722
Asp Phe Trp Phe Glu Ile Phe Asp Met Lys Lys Trp Asp Gln Phe Tyr
                225                 230                 235 agt gaa gtt cta gga aga ccc act aca tta tct gag aca atg ggg aaa        770
Ser Glu Val Leu Gly Arg Pro Thr Thr Leu Ser Glu Thr Met Gly Lys
            240                 245                 250 gct gac gta tgg ctt att cga aac tcc tgg aat ttt cag ttt cca tat        818
Ala Asp Val Trp Leu Ile Arg Asn Ser Trp Asn Phe Gln Phe Pro Tyr
        255                 260                 265 cca ctc tta cca aat gtt gat ttt gtt gga gga ctc cac tgc aaa cct        866
Pro Leu Leu Pro Asn Val Asp Phe Val Gly Gly Leu His Cys Lys Pro
    270                 275                 280 gcc aaa ccc ctg cct aag gaa atg gaa gac ttt gta cag agc tct gga        914
Ala Lys Pro Leu Pro Lys Glu Met Glu Asp Phe Val Gln Ser Ser Gly
285                 290                 295                 300 gaa aat ggt gtt gtg gtg ttt tct ctg ggg tca atg gtc agt aac atg        962
Glu Asn Gly Val Val Val Phe Ser Leu Gly Ser Met Val Ser Asn Met
                305                 310                 315 aca gaa gaa agg gcc aac gta att gca tca gcc ctg gcc cag atc cca       1010
Thr Glu Glu Arg Ala Asn Val Ile Ala Ser Ala Leu Ala Gln Ile Pro
            320                 325                 330 caa aag gtt ctg tgg aga ttt gat ggg aat aaa cca gat acc tta ggt       1058
Gln Lys Val Leu Trp Arg Phe Asp Gly Asn Lys Pro Asp Thr Leu Gly
        335                 340                 345 ctc aat act cgg ctc tac aag tgg ata ccc cag aat gac ctt cta ggt       1106
Leu Asn Thr Arg Leu Tyr Lys Trp Ile Pro Gln Asn Asp Leu Leu Gly
    350                 355                 360 cat cca aag acc aga gct ttt ata act cat ggt gga gcc aat ggc atc       1154
His Pro Lys Thr Arg Ala Phe Ile Thr His Gly Gly Ala Asn Gly Ile
365                 370                 375                 380 tac gag gca atc tac cat ggg atc cct atg gtg ggg att cca ttg ttt       1202
Tyr Glu Ala Ile Tyr His Gly Ile Pro Met Val Gly Ile Pro Leu Phe
                385                 390                 395 gcc gat caa cct gat aac att gct cac atg aag gcc agg gga gca gct       1250
Ala Asp Gln Pro Asp Asn Ile Ala His Met Lys Ala Arg Gly Ala Ala
            400                 405                 410 gtt aga gtg gac ttc aac aca atg tcg agt aca gac ttg ctg aat gca       1298
Val Arg Val Asp Phe Asn Thr Met Ser Ser Thr Asp Leu Leu Asn Ala
        415                 420                 425 ttg aag aga gta att aat gat cct tca tat aaa gag aat gtt atg aaa       1346
Leu Lys Arg Val Ile Asn Asp Pro Ser Tyr Lys Glu Asn Val Met Lys
    430                 435                 440
```

-continued

```
tta tca aga att caa cat gat caa cca gtg aag ccc ctg gat cga gca    1394
Leu Ser Arg Ile Gln His Asp Gln Pro Val Lys Pro Leu Asp Arg Ala
445                 450                 455                 460 gtc ttc tgg att gaa ttt gtc atg cgc cac aaa gga gct aaa cac ctt    1442
Val Phe Trp Ile Glu Phe Val Met Arg His Lys Gly Ala Lys His Leu
            465                 470                 475 cgg gtt gca gcc cac gac ctc acc tgg ttc cag tac cac tct ttg gat    1490
Arg Val Ala Ala His Asp Leu Thr Trp Phe Gln Tyr His Ser Leu Asp
        480                 485                 490 gtg att ggg ttc ctg ctg gtc tgt gtg gca act gtg ata ttt atc gtc    1538
Val Ile Gly Phe Leu Leu Val Cys Val Ala Thr Val Ile Phe Ile Val
    495                 500                 505 aca aaa tgt tgt ctg ttt tgt ttc tgg aag ttt gct aga aaa gca a      1584
Thr Lys Cys Cys Leu Phe Cys Phe Trp Lys Phe Ala Arg Lys Ala
510                 515                 520 agaagggaaa aaatgattag ttatatctga gatttgaagc tggaaaacct gataggtgag   1644
actacttcag tttattccag caagaaagat tgtgatgcaa gatttctttc ttcctgagac   1704
aaaaaaaaaa aaagaaaaaa aaatctttc aaaatttact ttgtcaaata aaatttgtt    1764 tttcagagat ttaccaccca gttcatggtt agaaatattt tgtggcaatg aagaaaacac   1824
tacggaaaat aaaaaataag ataaagcctt                                   1854
```

<210> SEQ ID NO 40
<211> LENGTH: 524
<212> TYPE: PRT
<213> ORGANISM: H. sapiens

<400> SEQUENCE: 40

```
Met Ser Val Lys Trp Thr Ser Val Ile Leu Leu Ile Gln Leu Ser Phe
1               5                   10                  15

Cys Phe Ser Ser Gly Asn Cys Gly Lys Val Leu Val Trp Ala Ala Glu
            20                  25                  30

Tyr Ser His Trp Met Asn Ile Lys Thr Ile Leu Asp Glu Leu Ile Gln
        35                  40                  45

Arg Gly His Glu Val Thr Val Leu Ala Ser Ser Ala Ser Ile Leu Phe
    50                  55                  60

Asp Pro Asn Asn Ser Ser Ala Leu Lys Ile Glu Ile Tyr Pro Thr Ser
65                  70                  75                  80

Leu Thr Lys Thr Glu Leu Glu Asn Phe Ile Met Gln Ile Lys Arg
                85                  90                  95

Trp Ser Asp Leu Pro Lys Asp Thr Phe Trp Leu Tyr Phe Ser Gln Val
            100                 105                 110

Gln Glu Ile Met Ser Ile Phe Gly Asp Ile Thr Arg Lys Phe Cys Lys
        115                 120                 125

Asp Val Val Ser Asn Lys Lys Phe Met Lys Val Gln Glu Ser Arg
130                 135                 140

Phe Asp Val Ile Phe Ala Asp Ala Ile Phe Pro Cys Ser Glu Leu Leu
145                 150                 155                 160

Ala Glu Leu Phe Asn Ile Pro Phe Val Tyr Ser Leu Ser Phe Ser Pro
                165                 170                 175

Gly Tyr Thr Phe Glu Lys His Ser Gly Gly Phe Ile Phe Pro Pro Ser
            180                 185                 190

Tyr Val Pro Val Val Met Ser Glu Leu Thr Asp Gln Met Thr Phe Met
        195                 200                 205

Glu Arg Val Lys Asn Met Ile Tyr Val Leu Tyr Phe Asp Phe Trp Phe
    210                 215                 220
```

Glu Ile Phe Asp Met Lys Lys Trp Asp Gln Phe Tyr Ser Glu Val Leu
225                 230                 235                 240

Gly Arg Pro Thr Thr Leu Ser Glu Thr Met Gly Lys Ala Asp Val Trp
            245                 250                 255

Leu Ile Arg Asn Ser Trp Asn Phe Gln Phe Pro Tyr Pro Leu Leu Pro
            260                 265                 270

Asn Val Asp Phe Val Gly Gly Leu His Cys Lys Pro Ala Lys Pro Leu
            275                 280                 285

Pro Lys Glu Met Glu Asp Phe Val Gln Ser Ser Gly Glu Asn Gly Val
        290                 295                 300

Val Val Phe Ser Leu Gly Ser Met Val Ser Asn Met Thr Glu Glu Arg
305                 310                 315                 320

Ala Asn Val Ile Ala Ser Ala Leu Ala Gln Ile Pro Gln Lys Val Leu
                325                 330                 335

Trp Arg Phe Asp Gly Asn Lys Pro Asp Thr Leu Gly Leu Asn Thr Arg
            340                 345                 350

Leu Tyr Lys Trp Ile Pro Gln Asn Asp Leu Leu Gly His Pro Lys Thr
        355                 360                 365

Arg Ala Phe Ile Thr His Gly Gly Ala Asn Gly Ile Tyr Glu Ala Ile
370                 375                 380

Tyr His Gly Ile Pro Met Val Gly Ile Pro Leu Phe Ala Asp Gln Pro
385                 390                 395                 400

Asp Asn Ile Ala His Met Lys Ala Arg Gly Ala Ala Val Arg Val Asp
                405                 410                 415

Phe Asn Thr Met Ser Ser Thr Asp Leu Leu Asn Ala Leu Lys Arg Val
            420                 425                 430

Ile Asn Asp Pro Ser Tyr Lys Glu Asn Val Met Lys Leu Ser Arg Ile
        435                 440                 445

Gln His Asp Gln Pro Val Lys Pro Leu Asp Arg Ala Val Phe Trp Ile
    450                 455                 460

Glu Phe Val Met Arg His Lys Gly Ala Lys His Leu Arg Val Ala Ala
465                 470                 475                 480

His Asp Leu Thr Trp Phe Gln Tyr His Ser Leu Asp Val Ile Gly Phe
            485                 490                 495

Leu Leu Val Cys Val Ala Thr Val Ile Phe Ile Val Thr Lys Cys Cys
            500                 505                 510

Leu Phe Cys Phe Trp Lys Phe Ala Arg Lys Ala Lys
            515                 520

<210> SEQ ID NO 41
<211> LENGTH: 1686
<212> TYPE: DNA
<213> ORGANISM: H. sapiens
<220> FEATURE:
<221> NAME/KEY: exon
<222> LOCATION: (392)...(1126)

<400> SEQUENCE: 41
tccccagttt cacaaaaata tgtggaccat gtttagtcat ttaatcttta gttttgtgtc      60
aaatggactg cagaaacaag atctgtcact gctactgttc tggacactct tctaaaatat    120
attgcataag acagatggca tgtccataca agatccttga tattagctga aggatagcac    180
tcataaacat aaaaggggaaa ttaatcacat ctgtgtgaac agatcattta ccttcatttg    240
tctctttgcc atccacatgc tcagactgtt gatttaatga tattgtatgt actttgactt    300

```
ataagggtta catttttaact tcttggctaa tttatctttg gacataacca tgagaaatga      360
cagaaaggaa cagcaactgg aaaacaagca ttgcattgca ccaggatgtc tgtgaaatgg      420
acttcagtaa ttttgctaat acaactgagc ttttgctttta gctctgggaa ttgtggaaag     480
gtgctggtgt gggcagcaga atacagccat tggatgaata taaagacaat cctggatgag     540
cttattcaga gaggtcatga ggtgactgta ctggcatctt cagcttccat tcttttttgat    600 cccaacaact catccgctct taaaattgaa atttatccca catctttaac taaaactgag     660
ttggagaatt tcatcatgca acagattaag agatggtcag accttccaaa agatacattt     720
tggttatatt tttcacaagt acaggaaatc atgtcaatat ttggtgacat aactagaaag     780
ttctgtaaag atgtagtttc aaataagaaa tttatgaaaa aagtacaaga gtcaagatttt    840 gacgtcattt ttgcagatgc tattttttccc tgtagtgagc tgctggctga gctatttaac   900 atacccttttg tgtacagtct cagcttctct cctggctaca cttttgaaaa gcatagtgga   960
ggatttattt tccctccttc ctacgtacct gttgttatgt cagaattaac tgatcaaatg    1020
actttcatgg agagggtaaa aaatatgatc tatgtgctttt actttgactt ttggttcgaa   1080
atatttgaca tgaagaagtg ggatcagttt tatagtgaag ttctaggtaa gtatttttttt   1140 caatcagtaa catgaagctc taacttattt gtgtctttga agcagagctt atataaagcc    1200
ataaagtcag ggtagtgggg ttttggtaag tgaatttata aaacaaaaat acaagatgat    1260
ctattaatct cacaaatatt atagaaaagc ttaaattaca gggtcagtta aaaccctgtg    1320
gccatcactc acacagaaca ccccaggaaa tcataaaacct atacattagt gcatctaaga   1380
ctttaagcaa ttacacatct gttttactat acattgtttt acatcttaaa aacagtaaaa    1440
tccatcaaat aacttcttac tgaatgcata gatttagaat gagtagttac acattttttct   1500 acaactatct atataactgc agaaattgtt ttttcttgta aacttgtttt cttatttaga    1560
aatcaaaaga tgttcccata ttaccagaag gtttccttca cagtaaagag agataatgtc    1620
tatacctcag atgcaaaaat caataagggc aatttgaagt ttctaatgtt tctatactct    1680
tgcagg                                                              1686
```

<210> SEQ ID NO 42
<211> LENGTH: 1340
<212> TYPE: DNA
<213> ORGANISM: H. sapiens
<220> FEATURE:
<221> NAME/KEY: exon
<222> LOCATION: (668)...(816)

<400> SEQUENCE: 42

```
atagtttttg gaactaggcc cctttattag aacatatgag acaattaagg tggagtacaa       60 ttttttatttc ataatttctc aaaaatttct agctataatg tacaaatata tttacttaaa     120
aatattatta agatcttagc ttgaatctaa agagtagtt ggtacaagga tttcagccat       180
actctcaaca tagtccacag ttcacttgaa ccaaagataa aagaattagc ttaatgagtt     240
gtgtaaacta gactatttct tagaaaatta tttttatggg tagagtagaa ttaattgatt     300
atggagctca aagagttgtt taaatgtccg tatgctacta ttgaagcttt aagagaaaag     360
aaattttatg tttaactttc tatggctcat tttaataatt gtttatgatt atgagcatac     420
tgatgcgaca ttagagatgt agcttaacct cacaattctc ctactacttttt gtctttctta   480 taaatacaca tgggcaaaat atgtaataca taaaattaaa ttatatctat atatgaatat     540
gtgtatatat ttttcaaagc acagatattt gcctacattt ttgcctacat tattctaacc     600
```

-continued

| | |
|---|---|
| cctttcagaa atttacctaa agtaattatc ttgtgtcatc cacctttttt ttttctattc | 660 |
| ctgtcaggaa gacccactac attatctgag acaatgggga aagctgacgt atggcttatt | 720 |
| cgaaactcct ggaattttca gtttccatat ccactcttac caaatgttga ttttgttgga | 780 |
| ggactccact gcaaacctgc caaacccctg cctaaggtaa acatactttt gttggtttta | 840 |
| ttttgttggc tttgaatttt cagtagaaat gattctatag tcttctttca gagtgtttga | 900 |
| cttacactga agaaagatg ggaaatgggt ggggtaaagc agataccaat tagaaactca | 960 |
| tgtgcacgtt aataccatca cacgtatatg agttttatga gtattacaaa tagagaggaa | 1020 |
| tactaaggag actttgaaaa tagggttggt taaattaaag tcttcattat gcaataccta | 1080 |
| agaaggtatt ggtcatccaa tcaaataata tttacaaagg gattagcaca aaacacaggt | 1140 |
| aagtgcagaa ttttcagaga aaaaaataga cacagtttct gtccccacat accttacatt | 1200 |
| ctacttcaaa agatagaata tgtgcaagta ataaaaaatta tataaaaact attatctgaa | 1260 |
| ggaaaaacgc aataccaaga aagcatcagt ggagataata gaaagtatcc tgcagtcact | 1320 |
| gattagtaag atgggtaccg | 1340 |

<210> SEQ ID NO 43
<211> LENGTH: 1822
<212> TYPE: DNA
<213> ORGANISM: H. sapiens
<220> FEATURE:
<221> NAME/KEY: exon
<222> LOCATION: (732)...(863)

<400> SEQUENCE: 43

| | |
|---|---|
| tatatacaat gtctgtatga taaatgagac tcctggcact aattcataga aattccaaat | 60 |
| tacattacca gactccagaa tgtcagcggt tcttaaccac cagcttttat ttattttatt | 120 |
| tttttagtt tttgaaaaac taccagaaaa ctctgaacaa actttaagtg aagtataaag | 180 |
| cattgtagag aaacataaat gtagatataa aattatccca actgtgagta gcttatcctc | 240 |
| agagctcata gttagggaag taaaccacta actgtttcca actaagagaa ttctacagaa | 300 |
| aacctgcctg aaataaacac aagggattta gtagaacaac aatataggat taaagctgag | 360 |
| tggtcccact ttccaagaac ctatattagt aactttagta atgaaagtga agagtcgtgt | 420 |
| attaatattt ttaacattat ctccctgaca acaatgtaat agctccattt cttttctccc | 480 |
| ttacacacat gcacacaaat acatacacat acacacatat ttacacaaat atccttaaca | 540 |
| gcatccacct atctcatatt atacatctac ttgcaaaaaa actgagtgat tgggtcagtt | 600 |
| aaaaaatatt atttactcca ataattcctc aaaatactgg attttctctc tttagtaatt | 660 |
| tgcaccaatt cttttggtag tgcccgctgt gctaatactc ttttgtgatg aagcaaattc | 720 |
| tttcttcaca ggaaatggaa gactttgtac agagctctgg agaaaatggt gttgtggtgt | 780 |
| tttctctggg gtcaatggtc agtaacatga cagaagaaag ggccaacgta attgcatcag | 840 |
| ccctggccca gatcccacaa aaggtaagat gaagtgcctt actggtgtgg aaaactactg | 900 |
| aaagaggctg ttaaagtttg aagtaatcca attatagaaa cttctgataa atgtgaagtt | 960 |
| gaccaaaagt tgaaaaatta gaacaaggat aatcttggag aaactatgag aagtttgaaa | 1020 |
| attgtggttg catttttttt taaatggtgt taagtatgaa cattccccta tgtaaatatg | 1080 |
| ctgacaataa attgaatgga gaaaggtatt taaaaagtgt ttggagactt ctcacctcct | 1140 |
| gtccataaaa ttttgaattg tgtatgtgat ctacatagga aaggatatta aagagtagat | 1200 |
| tgaactcttc catagctgaa tatagcctta aatatgcttg tatagcatcc accgacagaa | 1260 |

```
gtaatagttg tgcctcagac ttaggggttg catgtggccc tggaggagtt actacccttg    1320
gtatgcatga gtagttccta ttagcatcag tgggaactca gtactccata tgtattcaca    1380
aaaggcaact tgagacccac agttattttt aatttctgat attaacactc atacatactg    1440
ctgaatttaa ctcaatatat ttcagttaag tgaaaatggt gcttaatgta gtctttagaa    1500
tgactttcag gtgttttcac aaaaaacgta tatccagaac tgtgtccttt tagaaataca    1560
agtaaaattt tgataatta gcttcaaaac agttttccta atctcagcag tatccaatga    1620
gtgaagaaca cttgactgac tcttgggtca cctctattac ttattgtact ctggaagctc    1680
ttggtgaatg tttacgatta tgggatgtag tatttctgtt tgcactttaa gtcaaatgct    1740
tgtataaaat acgtgacaac aaatggagaa tattggctct gttagtagtt atgcggtata    1800
ttctctgttt aaggatcttt gg                                              1822

<210> SEQ ID NO 44
<211> LENGTH: 1591
<212> TYPE: DNA
<213> ORGANISM: H. sapiens
<220> FEATURE:
<221> NAME/KEY: exon
<222> LOCATION: (138)...(225)
<221> NAME/KEY: exon
<222> LOCATION: (1067)...(1286)

<400> SEQUENCE: 44
attctattta cattagcctt tgagtagttc ttatttacta acatcccttg atctcattcc      60
tactctttat acagttctca cattctataa cttttgaatt ccactcatgg aataaaatat     120 tttcttatt gtaacaggtt ctgtggagat ttgatgggaa taaaccagat accttaggtc     180
tcaatactcg gctctacaag tggatacccc agaatgacct tctaggtaag actctggtga    240
acaaatactg aatatattag taacagcaca ttagagtgtt aatagttcat catgaaacaa    300
gcttattgaa tatttgttaa ggaaaaacaa aatgtaactt ctttatattg attttccagt    360
cttaagggag aaagaataca ttataatttt tggcatttta tgatatacac ccacattctt    420
tatagtctga atcgggggaa tctttatttc aggtgttatt atatctcaca aaatttttca    480
ataacttcct gggctgtctc tctgtctcct atttctacaa cttttacacct gttttttttcc    540 tctcccgcag ggttatttga aatgccacta aaaataatag ctcttctatc accagtgact    600
ctgtattttc tgaagaatta aactgctaat cttaatcata cagtgatgat acatttcacg    660
atgaagtgtg acctgtcctt cctcaatcct agcaccacca ccaaaccact gcctgctgcc    720
ttgcccaccc catatatcac actctgtgac tgtcacttaa aataagagtt cacttcatgc    780
ctatctcttt gctgtcttct tttttgcaca ttttttgaaat ctagaatgca attttttcatt    840 agcccaactg gaaatcttgt attgttttgc agtctgaagt cacacacacc gtatagcctt    900
cagttacata cccagtacaa gtacgtgttt tttcctccga agtctgaaac acaatttttaa    960 tttagttcag tgttttagct ggaaaacact gtcactttca gagcctttca ttgtgcatct   1020
cattttattc ctatgagtaa ttttgctaaa attcatccaa tcctaggtca tccaaagacc   1080
agagctttta taactcatgg tggagccaat ggcatctacg aggcaatcta ccatgggatc   1140
cctatggtgg ggattccatt gttgccgat caacctgata acattgctca catgaaggcc   1200 agggagcag ctgttagagt ggacttcaac acaatgtcga gtacagactt gctgaatgca   1260
ttgaagagag taattaatga tccttcgtga gtagaacaat atttttcact aggtggtatt   1320
tacagatagc ttctcttgtc aatagtgagt gtgagtttca tccttttttat aagagactaa   1380
```

-continued

```
ttttgaaaga atttaatgat ttaaccaatc tgaaatctgc ttttattttt ataagttatt    1440
taaaaattga atttgaaaca catacatcta aagaatagcc agttagtgaa acaattttct    1500
acacaaaaat aattttaaaa ggatatagat aatacaaaaa atacatttct taaaaatttg    1560
acataattaa tccatagaag aaaggaagaa t                                   1591
```

<210> SEQ ID NO 45
<211> LENGTH: 596
<212> TYPE: DNA
<213> ORGANISM: H. sapiens
<220> FEATURE:
<221> NAME/KEY: exon
<222> LOCATION: (19)...(549)

<400> SEQUENCE: 45

```
ctttattttt atctttcaga tataaagaga atgttatgaa attatcaaga attcaacatg     60
atcaaccagt gaagcccctg gatcgagcag tcttctggat tgaatttgtc atgcgccaca    120
aaggagctaa acaccttcgg gttgcagccc acgacctcac ctggttccag taccactctt    180
tggatgtgat tgggttcctg ctggtctgtg tggcaactgt gatatttatc gtcacaaaat    240
gttgtctgtt ttgtttctgg aagtttgcta gaaaagcaaa gaagggaaaa atgattagt     300 tatatctgag atttgaagct ggaaaacctg ataggtgaga ctacttcagt ttattccagc    360
aagaaagatt gtgatgcaag atttctttct tcctgagaca aaaaaaaaaa aagaaaaaaa    420
aatcttttca aaatttactt tgtcaaataa aaatttgttt ttcagagatt taccacccag    480
ttcatggtta gaaatatttt gtggcaatga agaaaacact acggaaaata aaaaataaga    540
taaagcctta tgagctcgta ttgaaatttg ttgaacttat atcgcggatc ctactg        596
```

<210> SEQ ID NO 46
<211> LENGTH: 20
<212> TYPE: DNA
<213> ORGANISM: H. sapiens

<400> SEQUENCE: 46

```
cttggctaat ttatctttgg                                                 20
```

<210> SEQ ID NO 47
<211> LENGTH: 19
<212> TYPE: DNA
<213> ORGANISM: H. sapiens

<400> SEQUENCE: 47

```
cccactaccc tgactttat                                                  19
```

<210> SEQ ID NO 48
<211> LENGTH: 20
<212> TYPE: DNA
<213> ORGANISM: H. sapiens

<400> SEQUENCE: 48

```
ggacataacc atgagaaatg                                                 20
```

<210> SEQ ID NO 49
<211> LENGTH: 19
<212> TYPE: DNA
<213> ORGANISM: H. sapiens

<400> SEQUENCE: 49

```
agctctgctt caaagacac                                                  19
```

<210> SEQ ID NO 50
<211> LENGTH: 21
<212> TYPE: DNA
<213> ORGANISM: H. sapiens

<400> SEQUENCE: 50
tgtccgtatg ctactattga a                                          21

<210> SEQ ID NO 51
<211> LENGTH: 21
<212> TYPE: DNA
<213> ORGANISM: H. sapiens

<400> SEQUENCE: 51
tgtgctaatc cctttgtaaa t                                          21

<210> SEQ ID NO 52
<211> LENGTH: 22
<212> TYPE: DNA
<213> ORGANISM: H. sapiens

<400> SEQUENCE: 52 ttttttttc tattcctgtc ag                                          22

<210> SEQ ID NO 53
<211> LENGTH: 17
<212> TYPE: DNA
<213> ORGANISM: H. sapiens

<400> SEQUENCE: 53
ctttacccca cccattt                                               17

<210> SEQ ID NO 54
<211> LENGTH: 20
<212> TYPE: DNA
<213> ORGANISM: H. sapiens

<400> SEQUENCE: 54
cccttgatct cattcctact                                            20

<210> SEQ ID NO 55
<211> LENGTH: 24
<212> TYPE: DNA
<213> ORGANISM: H. sapiens

<400> SEQUENCE: 55
aactggctat tctttagatg tatg                                       24

<210> SEQ ID NO 56
<211> LENGTH: 25
<212> TYPE: DNA
<213> ORGANISM: H. sapiens

<400> SEQUENCE: 56
cattcctact ctttatacag ttctc                                      25

<210> SEQ ID NO 57
<211> LENGTH: 17
<212> TYPE: DNA
<213> ORGANISM: H. sapiens

<400> SEQUENCE: 57
cccccgattc agactat                                               17

<210> SEQ ID NO 58
<211> LENGTH: 20
<212> TYPE: DNA
<213> ORGANISM: H. sapiens

<400> SEQUENCE: 58
cccttgatct cattcctact                                              20

<210> SEQ ID NO 59
<211> LENGTH: 24
<212> TYPE: DNA
<213> ORGANISM: H. sapiens

<400> SEQUENCE: 59
aactggctat tctttagatg tatg                                         24

<210> SEQ ID NO 60
<211> LENGTH: 18
<212> TYPE: DNA
<213> ORGANISM: H. sapiens

<400> SEQUENCE: 60
tcctccgaag tctgaaac                                                18

<210> SEQ ID NO 61
<211> LENGTH: 23
<212> TYPE: DNA
<213> ORGANISM: H. sapiens

<400> SEQUENCE: 61
tataaaaagg atgaaactca cac                                          23

<210> SEQ ID NO 62
<211> LENGTH: 18
<212> TYPE: DNA
<213> ORGANISM: H. sapiens

<400> SEQUENCE: 62
caagccccca agttatgt                                                18

<210> SEQ ID NO 63
<211> LENGTH: 20
<212> TYPE: DNA
<213> ORGANISM: H. sapiens

<400> SEQUENCE: 63
cagtaggatc cgcgatataa                                              20

<210> SEQ ID NO 64
<211> LENGTH: 20
<212> TYPE: DNA
<213> ORGANISM: H. sapiens

<400> SEQUENCE: 64 tctgagggt tttgtctgta                                               20

<210> SEQ ID NO 65
<211> LENGTH: 20
<212> TYPE: DNA
<213> ORGANISM: H. sapiens

<400> SEQUENCE: 65

```
ccgcgatata agttcaacaa                                              20

<210> SEQ ID NO 66
<211> LENGTH: 20
<212> TYPE: DNA
<213> ORGANISM: H. sapiens

<400> SEQUENCE: 66
ggacataacc atgagaaatg                                              20

<210> SEQ ID NO 67
<211> LENGTH: 19
<212> TYPE: DNA
<213> ORGANISM: H. sapiens

<400> SEQUENCE: 67
ttaagagcgg atgagttgt                                               19

<210> SEQ ID NO 68
<211> LENGTH: 20
<212> TYPE: DNA
<213> ORGANISM: H. sapiens

<400> SEQUENCE: 68
tcatcatgca acagattaag                                              20

<210> SEQ ID NO 69
<211> LENGTH: 20
<212> TYPE: DNA
<213> ORGANISM: H. sapiens

<400> SEQUENCE: 69
cactacaggg aaaaatagca                                              20

<210> SEQ ID NO 70
<211> LENGTH: 20
<212> TYPE: DNA
<213> ORGANISM: H. sapiens

<400> SEQUENCE: 70 acccttttgtg tacagtctca                                             20

<210> SEQ ID NO 71
<211> LENGTH: 19
<212> TYPE: DNA
<213> ORGANISM: H. sapiens

<400> SEQUENCE: 71
agctctgctt caaagacac                                               19

<210> SEQ ID NO 72
<211> LENGTH: 21
<212> TYPE: DNA
<213> ORGANISM: H. sapiens

<400> SEQUENCE: 72
ttgcctacat tattctaacc c                                            21

<210> SEQ ID NO 73
<211> LENGTH: 17
<212> TYPE: DNA
<213> ORGANISM: H. sapiens

<400> SEQUENCE: 73
```

```
ctttacccca cccattt                                          17

<210> SEQ ID NO 74
<211> LENGTH: 25
<212> TYPE: DNA
<213> ORGANISM: H. sapiens

<400> SEQUENCE: 74
cattcctact ctttatacag ttctc                                 25

<210> SEQ ID NO 75
<211> LENGTH: 17
<212> TYPE: DNA
<213> ORGANISM: H. sapiens

<400> SEQUENCE: 75
cccccgattc agactat                                          17

<210> SEQ ID NO 76
<211> LENGTH: 25
<212> TYPE: DNA
<213> ORGANISM: H. sapiens

<400> SEQUENCE: 76
cattcctact ctttatacag ttctc                                 25

<210> SEQ ID NO 77
<211> LENGTH: 17
<212> TYPE: DNA
<213> ORGANISM: H. sapiens

<400> SEQUENCE: 77
cccccgattc agactat                                          17

<210> SEQ ID NO 78
<211> LENGTH: 18
<212> TYPE: DNA
<213> ORGANISM: H. sapiens

<400> SEQUENCE: 78
tcctccgaag tctgaaac                                         18

<210> SEQ ID NO 79
<211> LENGTH: 23
<212> TYPE: DNA
<213> ORGANISM: H. sapiens

<400> SEQUENCE: 79
tataaaaagg atgaaactca cac                                   23

<210> SEQ ID NO 80
<211> LENGTH: 20
<212> TYPE: DNA
<213> ORGANISM: H. sapiens

<400> SEQUENCE: 80
tctgaggggt tttgtctgta                                       20

<210> SEQ ID NO 81
<211> LENGTH: 22
<212> TYPE: DNA
<213> ORGANISM: H. sapiens
```

-continued

```
<400> SEQUENCE: 81 tttttgtct caggaagaaa ga                                              22

<210> SEQ ID NO 82
<211> LENGTH: 24
<212> TYPE: DNA
<213> ORGANISM: H. sapiens

<400> SEQUENCE: 82 aaaaaagaa aaaaaatct tttc                                             24

<210> SEQ ID NO 83
<211> LENGTH: 20
<212> TYPE: DNA
<213> ORGANISM: H. sapiens

<400> SEQUENCE: 83
ccgcgatata agttcaacaa                                                20

<210> SEQ ID NO 84
<211> LENGTH: 22
<212> TYPE: DNA
<213> ORGANISM: H. sapiens

<400> SEQUENCE: 84
tgcattgcac caggatgtct gt                                             22

<210> SEQ ID NO 85
<211> LENGTH: 21
<212> TYPE: DNA
<213> ORGANISM: H. sapiens

<400> SEQUENCE: 85
gcattgcacc aagatgtctg t                                              21

<210> SEQ ID NO 86
<211> LENGTH: 23
<212> TYPE: DNA
<213> ORGANISM: H. sapiens

<400> SEQUENCE: 86
tcctggatga gcttattcag aga                                            23

<210> SEQ ID NO 87
<211> LENGTH: 23
<212> TYPE: DNA
<213> ORGANISM: H. sapiens

<400> SEQUENCE: 87
tcctggatga gcctattcag aga                                            23

<210> SEQ ID NO 88
<211> LENGTH: 21
<212> TYPE: DNA
<213> ORGANISM: H. sapiens

<400> SEQUENCE: 88
cattttggtt atattttca c                                               21

<210> SEQ ID NO 89
<211> LENGTH: 21
<212> TYPE: DNA
<213> ORGANISM: H. sapiens
```

```
<400> SEQUENCE: 89
cattttggtt ttattttca c                                          21

<210> SEQ ID NO 90
<211> LENGTH: 21
<212> TYPE: DNA
<213> ORGANISM: H. sapiens

<400> SEQUENCE: 90
cataactaga aagttctgta a                                         21

<210> SEQ ID NO 91
<211> LENGTH: 21
<212> TYPE: DNA
<213> ORGANISM: H. sapiens

<400> SEQUENCE: 91
cataactagg aagttctgta a                                         21

<210> SEQ ID NO 92
<211> LENGTH: 20
<212> TYPE: DNA
<213> ORGANISM: H. sapiens

<400> SEQUENCE: 92
cctggctaca cttttgaaaa                                           20

<210> SEQ ID NO 93
<211> LENGTH: 20
<212> TYPE: DNA
<213> ORGANISM: H. sapiens

<400> SEQUENCE: 93
cctggctaca ttttgaaaa                                            20

<210> SEQ ID NO 94
<211> LENGTH: 21
<212> TYPE: DNA
<213> ORGANISM: H. sapiens

<400> SEQUENCE: 94
gaagacccac tacattatct g                                         21

<210> SEQ ID NO 95
<211> LENGTH: 21
<212> TYPE: DNA
<213> ORGANISM: H. sapiens

<400> SEQUENCE: 95
gaagacccac tacgttatct g                                         21

<210> SEQ ID NO 96
<211> LENGTH: 26
<212> TYPE: DNA
<213> ORGANISM: H. sapiens

<400> SEQUENCE: 96
aattttcagt ttccatatcc actctt                                    26

<210> SEQ ID NO 97
<211> LENGTH: 26
<212> TYPE: DNA
```

```
<213> ORGANISM: H. sapiens

<400> SEQUENCE: 97
aattttcagt ttcctcatcc actctt                                         26

<210> SEQ ID NO 98
<211> LENGTH: 22
<212> TYPE: DNA
<213> ORGANISM: H. sapiens

<400> SEQUENCE: 98
taggtctcaa tactcggctc ta                                             22

<210> SEQ ID NO 99
<211> LENGTH: 22
<212> TYPE: DNA
<213> ORGANISM: H. sapiens

<400> SEQUENCE: 99
taggtctcaa tactcggctg ta                                             22

<210> SEQ ID NO 100
<211> LENGTH: 19
<212> TYPE: DNA
<213> ORGANISM: H. sapiens

<400> SEQUENCE: 100
tacaagtgga taccccaga                                                 19

<210> SEQ ID NO 101
<211> LENGTH: 19
<212> TYPE: DNA
<213> ORGANISM: H. sapiens

<400> SEQUENCE: 101
tataagtgga taccccaga                                                 19

<210> SEQ ID NO 102
<211> LENGTH: 26
<212> TYPE: DNA
<213> ORGANISM: H. sapiens

<400> SEQUENCE: 102
gggagaaaga atacattata attttt                                         26

<210> SEQ ID NO 103
<211> LENGTH: 25
<212> TYPE: DNA
<213> ORGANISM: H. sapiens

<400> SEQUENCE: 103
gggagaaaga atacttataa ttttt                                          25

<210> SEQ ID NO 104
<211> LENGTH: 21
<212> TYPE: DNA
<213> ORGANISM: H. sapiens

<400> SEQUENCE: 104
ttccattgtt tgccgatcaa c                                              21

<210> SEQ ID NO 105
<211> LENGTH: 21
```

```
<212> TYPE: DNA
<213> ORGANISM: H. sapiens

<400> SEQUENCE: 105
ttccattgtt tgctgatcaa c                                              21

<210> SEQ ID NO 106
<211> LENGTH: 21
<212> TYPE: DNA
<213> ORGANISM: H. sapiens

<400> SEQUENCE: 106
gaatgcattg aagagagtaa t                                              21

<210> SEQ ID NO 107
<211> LENGTH: 21
<212> TYPE: DNA
<213> ORGANISM: H. sapiens

<400> SEQUENCE: 107
gaatgcattg cagagagtaa t                                              21

<210> SEQ ID NO 108
<211> LENGTH: 22
<212> TYPE: DNA
<213> ORGANISM: H. sapiens

<400> SEQUENCE: 108
ctggtctgtg tggcaactgt ga                                             22

<210> SEQ ID NO 109
<211> LENGTH: 22
<212> TYPE: DNA
<213> ORGANISM: H. sapiens

<400> SEQUENCE: 109
ctggtctgtg tggcgactgt ga                                             22

<210> SEQ ID NO 110
<211> LENGTH: 19
<212> TYPE: DNA
<213> ORGANISM: H. sapiens

<400> SEQUENCE: 110
taagataaag ccttatgag                                                 19

<210> SEQ ID NO 111
<211> LENGTH: 19
<212> TYPE: DNA
<213> ORGANISM: H. sapiens

<400> SEQUENCE: 111
taagataaag acttatgag                                                 19

<210> SEQ ID NO 112
<211> LENGTH: 1976
<212> TYPE: DNA
<213> ORGANISM: H. sapiens
<220> FEATURE:
<221> NAME/KEY: CDS
<222> LOCATION: (11)...(1598)

<400> SEQUENCE: 112
taagaccagg atg tct ctg aaa tgg acg tca gtc ttt ctg ctg ata cag      49
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     | Met | Ser | Leu | Lys | Trp | Thr | Ser | Val | Phe | Leu | Leu | Ile | Gln |     |
|     |     | 1   |     |     |     | 5   |     |     |     |     | 10  |     |     |     |     |
| ctc | agt | tgt | tac | ttt | agc | tct | gga | agc | tgt | gga | aag | gtg | cta | gtg | tgg | 97 |
| Leu | Ser | Cys | Tyr | Phe | Ser | Ser | Gly | Ser | Cys | Gly | Lys | Val | Leu | Val | Trp |
| 15  |     |     |     |     | 20  |     |     |     |     | 25  |     |     |     |     |     |
| ccc | aca | gaa | tac | agc | cat | tgg | ata | aat | atg | aag | aca | atc | ctg | gaa | gag | 145 |
| Pro | Thr | Glu | Tyr | Ser | His | Trp | Ile | Asn | Met | Lys | Thr | Ile | Leu | Glu | Glu |
| 30  |     |     |     |     | 35  |     |     |     |     | 40  |     |     |     |     | 45  |
| ctt | gtt | cag | agg | ggt | cat | gag | gtg | act | gtg | ttg | aca | tct | tcg | gct | tct | 193 |
| Leu | Val | Gln | Arg | Gly | His | Glu | Val | Thr | Val | Leu | Thr | Ser | Ser | Ala | Ser |
|     |     |     |     | 50  |     |     |     |     | 55  |     |     |     |     | 60  |     |
| act | ctt | gtc | aat | gcc | agt | aaa | tca | tct | gct | att | aaa | tta | gaa | gtt | tat | 241 |
| Thr | Leu | Val | Asn | Ala | Ser | Lys | Ser | Ser | Ala | Ile | Lys | Leu | Glu | Val | Tyr |
|     |     |     |     | 65  |     |     |     |     | 70  |     |     |     |     | 75  |     |
| cct | aca | tct | tta | act | aaa | aat | gat | ttg | gaa | gat | tct | ctt | ctg | aaa | att | 289 |
| Pro | Thr | Ser | Leu | Thr | Lys | Asn | Asp | Leu | Glu | Asp | Ser | Leu | Leu | Lys | Ile |
|     |     |     | 80  |     |     |     |     | 85  |     |     |     |     | 90  |     |     |
| ctc | gat | aga | tgg | ata | tat | ggt | gtt | tca | aaa | aat | aca | ttt | tgg | tca | tat | 337 |
| Leu | Asp | Arg | Trp | Ile | Tyr | Gly | Val | Ser | Lys | Asn | Thr | Phe | Trp | Ser | Tyr |
|     | 95  |     |     |     |     | 100 |     |     |     |     | 105 |     |     |     |     |
| ttt | tca | caa | tta | caa | gaa | ttg | tgt | tgg | gaa | tat | tat | gac | tac | agt | aac | 385 |
| Phe | Ser | Gln | Leu | Gln | Glu | Leu | Cys | Trp | Glu | Tyr | Tyr | Asp | Tyr | Ser | Asn |
| 110 |     |     |     |     | 115 |     |     |     |     | 120 |     |     |     |     | 125 |
| aag | ctc | tgt | aaa | gat | gca | gtt | ttg | aat | aag | aaa | ctt | atg | atg | aaa | cta | 433 |
| Lys | Leu | Cys | Lys | Asp | Ala | Val | Leu | Asn | Lys | Lys | Leu | Met | Met | Lys | Leu |
|     |     |     |     | 130 |     |     |     |     | 135 |     |     |     |     | 140 |     |
| caa | gag | tca | aag | ttt | gat | gtc | att | ctg | gca | gat | gcc | ctt | aat | ccc | tgt | 481 |
| Gln | Glu | Ser | Lys | Phe | Asp | Val | Ile | Leu | Ala | Asp | Ala | Leu | Asn | Pro | Cys |
|     |     |     | 145 |     |     |     |     | 150 |     |     |     |     | 155 |     |     |
| ggt | gag | cta | ctg | gct | gaa | cta | ttt | aac | ata | ccc | ttt | ctg | tac | agt | ctt | 529 |
| Gly | Glu | Leu | Leu | Ala | Glu | Leu | Phe | Asn | Ile | Pro | Phe | Leu | Tyr | Ser | Leu |
|     |     | 160 |     |     |     |     | 165 |     |     |     |     | 170 |     |     |     |
| cga | ttc | tct | gtt | ggc | tac | aca | ttt | gag | aag | aat | ggt | gga | gga | ttt | ctg | 577 |
| Arg | Phe | Ser | Val | Gly | Tyr | Thr | Phe | Glu | Lys | Asn | Gly | Gly | Gly | Phe | Leu |
|     | 175 |     |     |     |     | 180 |     |     |     |     | 185 |     |     |     |     |
| ttc | cct | cct | tcc | tat | gta | cct | gtt | gtt | atg | tca | gaa | tta | agt | gat | caa | 625 |
| Phe | Pro | Pro | Ser | Tyr | Val | Pro | Val | Val | Met | Ser | Glu | Leu | Ser | Asp | Gln |
| 190 |     |     |     |     | 195 |     |     |     |     | 200 |     |     |     |     | 205 |
| atg | att | ttc | atg | gag | agg | ata | aaa | aat | atg | ata | cat | atg | ctt | tat | ttt | 673 |
| Met | Ile | Phe | Met | Glu | Arg | Ile | Lys | Asn | Met | Ile | His | Met | Leu | Tyr | Phe |
|     |     |     |     | 210 |     |     |     |     | 215 |     |     |     |     | 220 |     |
| gac | ttt | tgg | ttt | caa | att | tat | gat | ctg | aag | aag | tgg | gac | cag | ttt | tat | 721 |
| Asp | Phe | Trp | Phe | Gln | Ile | Tyr | Asp | Leu | Lys | Lys | Trp | Asp | Gln | Phe | Tyr |
|     |     |     | 225 |     |     |     |     | 230 |     |     |     |     | 235 |     |     |
| agt | gaa | gtt | cta | gga | aga | ccc | act | aca | tta | ttt | gag | aca | atg | ggg | aaa | 769 |
| Ser | Glu | Val | Leu | Gly | Arg | Pro | Thr | Thr | Leu | Phe | Glu | Thr | Met | Gly | Lys |
|     |     | 240 |     |     |     |     | 245 |     |     |     |     | 250 |     |     |     |
| gct | gaa | atg | tgg | ctc | att | cga | acc | tat | tgg | gat | ttt | gaa | ttt | cct | cgc | 817 |
| Ala | Glu | Met | Trp | Leu | Ile | Arg | Thr | Tyr | Trp | Asp | Phe | Glu | Phe | Pro | Arg |
|     | 255 |     |     |     |     | 260 |     |     |     |     | 265 |     |     |     |     |
| cca | ttc | tta | cca | aat | gtt | gat | ttt | gtt | gga | gga | ctt | cac | tgt | aaa | cca | 865 |
| Pro | Phe | Leu | Pro | Asn | Val | Asp | Phe | Val | Gly | Gly | Leu | His | Cys | Lys | Pro |
| 270 |     |     |     |     | 275 |     |     |     |     | 280 |     |     |     |     | 285 |
| gcc | aaa | ccc | ctg | cct | aag | gaa | atg | gaa | gag | ttt | gtg | cag | agc | tct | gga | 913 |
| Ala | Lys | Pro | Leu | Pro | Lys | Glu | Met | Glu | Glu | Phe | Val | Gln | Ser | Ser | Gly |
|     |     |     |     | 290 |     |     |     |     | 295 |     |     |     |     | 300 |     |
| gaa | aat | ggt | att | gtg | gtg | ttt | tct | ctg | ggg | tcg | atg | atc | agt | aac | atg | 961 |
| Glu | Asn | Gly | Ile | Val | Val | Phe | Ser | Leu | Gly | Ser | Met | Ile | Ser | Asn | Met |
|     |     |     | 305 |     |     |     |     | 310 |     |     |     |     | 315 |     |     |

```
                              -continued tca gaa gaa agt gcc aac atg att gca tca gcc ctt gcc cag atc cca    1009
Ser Glu Glu Ser Ala Asn Met Ile Ala Ser Ala Leu Ala Gln Ile Pro
        320                 325                 330 caa aag gtt cta tgg aga ttt gat ggc aag aag cca aat act tta ggt    1057
Gln Lys Val Leu Trp Arg Phe Asp Gly Lys Lys Pro Asn Thr Leu Gly
335                 340                 345 tcc aat act cga ctg tac aag tgg tta ccc cag aat gac ctt ctt ggt    1105
Ser Asn Thr Arg Leu Tyr Lys Trp Leu Pro Gln Asn Asp Leu Leu Gly
350                 355                 360                 365 cat ccc aaa acc aaa gct ttt ata act cat ggt gga acc aat ggc atc    1153
His Pro Lys Thr Lys Ala Phe Ile Thr His Gly Gly Thr Asn Gly Ile
                370                 375                 380 tat gag gcg atc tac cat ggg atc cct atg gtg ggc att ccc ttg ttt    1201
Tyr Glu Ala Ile Tyr His Gly Ile Pro Met Val Gly Ile Pro Leu Phe
        385                 390                 395 gcg gat caa cat gat aac att gct cac atg aaa gcc aag gga gca gcc    1249
Ala Asp Gln His Asp Asn Ile Ala His Met Lys Ala Lys Gly Ala Ala
    400                 405                 410 ctc agt gtg gac atc agg acc atg tca agt aga gat ttg ctc aat gca    1297
Leu Ser Val Asp Ile Arg Thr Met Ser Ser Arg Asp Leu Leu Asn Ala
415                 420                 425 ttg aag tca gtc att aat gac cct gtc tat aaa gag aat gtc atg aaa    1345
Leu Lys Ser Val Ile Asn Asp Pro Val Tyr Lys Glu Asn Val Met Lys
430                 435                 440                 445 tta tca aga att cat cat gac caa cca atg aag ccc ctg gat cga gca    1393
Leu Ser Arg Ile His His Asp Gln Pro Met Lys Pro Leu Asp Arg Ala
                450                 455                 460 gtc ttc tgg att gag ttt gtc atg cgc cac aaa gga gcc aag cac ctt    1441
Val Phe Trp Ile Glu Phe Val Met Arg His Lys Gly Ala Lys His Leu
        465                 470                 475 cga gtc gca gct cac aac ctc acc tgg atc cag tac cac tct ttg gat    1489
Arg Val Ala Ala His Asn Leu Thr Trp Ile Gln Tyr His Ser Leu Asp
    480                 485                 490 gtg ata gca ttc ctg ctg gcc tgc gtg gca act gtg ata ttt atc atc    1537
Val Ile Ala Phe Leu Leu Ala Cys Val Ala Thr Val Ile Phe Ile Ile
495                 500                 505 aca aaa ttt tgc ctg ttt tgt ttc cga aag ctt gcc aaa aca gga aag    1585
Thr Lys Phe Cys Leu Phe Cys Phe Arg Lys Leu Ala Lys Thr Gly Lys
510                 515                 520                 525 aag aag aaa aga g attagttata tcaaaagcct gaagtggaat gactgaaaga     1638
Lys Lys Lys Arg tgggactcct cctttatttc agcatggagg gttttaaatg gaggatttcc ttttcctgt   1698 gacaaaacat cttttcacta cttaccttgt taagacaaaa tttatttcc agggatttaa   1758 tacgtacttt agttggaatt attctatgtc aatgattttt aagctatgaa aaatacaatg  1818
gggggaagga tagcatttgg agatatacct aatgttaaat gacgagttac tggatgcagc  1878
acgccaacat ggcacatgta tacatatgta gctaacctca cgttgtgcac atgtacccta  1938
aaacttaaag tataatttaa aaaaagcaaa gggtaccg                         1976

<210> SEQ ID NO 113
<211> LENGTH: 530
<212> TYPE: PRT
<213> ORGANISM: H. sapiens

<400> SEQUENCE: 113

Met Ser Leu Lys Trp Thr Ser Val Phe Leu Leu Ile Gln Leu Ser Cys
1               5                   10                  15

Tyr Phe Ser Ser Gly Ser Cys Gly Lys Val Leu Val Trp Pro Thr Glu
```

-continued

```
            20                  25                  30
Tyr Ser His Trp Ile Asn Met Lys Thr Ile Leu Glu Glu Leu Val Gln
                35                  40                  45
Arg Gly His Glu Val Thr Val Leu Thr Ser Ser Ala Ser Thr Leu Val
 50                  55                  60
Asn Ala Ser Lys Ser Ser Ala Ile Lys Leu Glu Val Tyr Pro Thr Ser
65                  70                  75                  80
Leu Thr Lys Asn Asp Leu Glu Asp Ser Leu Leu Lys Ile Leu Asp Arg
                85                  90                  95
Trp Ile Tyr Gly Val Ser Lys Asn Thr Phe Trp Ser Tyr Phe Ser Gln
                100                 105                 110
Leu Gln Glu Leu Cys Trp Glu Tyr Tyr Asp Tyr Ser Asn Lys Leu Cys
                115                 120                 125
Lys Asp Ala Val Leu Asn Lys Lys Leu Met Met Lys Leu Gln Glu Ser
                130                 135                 140
Lys Phe Asp Val Ile Leu Ala Asp Ala Leu Asn Pro Cys Gly Glu Leu
145                 150                 155                 160
Leu Ala Glu Leu Phe Asn Ile Pro Phe Leu Tyr Ser Leu Arg Phe Ser
                165                 170                 175
Val Gly Tyr Thr Phe Glu Lys Asn Gly Gly Phe Leu Phe Pro Pro
                180                 185                 190
Ser Tyr Val Pro Val Met Ser Glu Leu Ser Asp Gln Met Ile Phe
                195                 200                 205
Met Glu Arg Ile Lys Asn Met Ile His Met Leu Tyr Phe Asp Phe Trp
                210                 215                 220
Phe Gln Ile Tyr Asp Leu Lys Lys Trp Asp Gln Phe Tyr Ser Glu Val
225                 230                 235                 240
Leu Gly Arg Pro Thr Thr Leu Phe Glu Thr Met Gly Lys Ala Glu Met
                245                 250                 255
Trp Leu Ile Arg Thr Tyr Trp Asp Phe Glu Phe Pro Arg Pro Phe Leu
                260                 265                 270
Pro Asn Val Asp Phe Val Gly Gly Leu His Cys Lys Pro Ala Lys Pro
                275                 280                 285
Leu Pro Lys Glu Met Glu Glu Phe Val Gln Ser Ser Gly Glu Asn Gly
                290                 295                 300
Ile Val Val Phe Ser Leu Gly Ser Met Ile Ser Asn Met Ser Glu Glu
305                 310                 315                 320
Ser Ala Asn Met Ile Ala Ser Ala Leu Ala Gln Ile Pro Gln Lys Val
                325                 330                 335
Leu Trp Arg Phe Asp Gly Lys Lys Pro Asn Thr Leu Gly Ser Asn Thr
                340                 345                 350
Arg Leu Tyr Lys Trp Leu Pro Gln Asn Asp Leu Leu Gly His Pro Lys
                355                 360                 365
Thr Lys Ala Phe Ile Thr His Gly Gly Thr Asn Gly Ile Tyr Glu Ala
                370                 375                 380
Ile Tyr His Gly Ile Pro Met Val Gly Ile Pro Leu Phe Ala Asp Gln
385                 390                 395                 400
His Asp Asn Ile Ala His Met Lys Ala Lys Gly Ala Ala Leu Ser Val
                405                 410                 415
Asp Ile Arg Thr Met Ser Ser Arg Asp Leu Leu Asn Ala Leu Lys Ser
                420                 425                 430
Val Ile Asn Asp Pro Val Tyr Lys Glu Asn Val Met Lys Leu Ser Arg
                435                 440                 445
```

```
Ile His His Asp Gln Pro Met Lys Pro Leu Asp Arg Ala Val Phe Trp
    450                 455                 460

Ile Glu Phe Val Met Arg His Lys Gly Ala Lys His Leu Arg Val Ala
465                 470                 475                 480

Ala His Asn Leu Thr Trp Ile Gln Tyr His Ser Leu Asp Val Ile Ala
                485                 490                 495

Phe Leu Leu Ala Cys Val Ala Thr Val Ile Phe Ile Ile Thr Lys Phe
            500                 505                 510

Cys Leu Phe Cys Phe Arg Lys Leu Ala Lys Thr Gly Lys Lys Lys Lys
        515                 520                 525

Arg Asp
    530
```

<210> SEQ ID NO 114
<211> LENGTH: 2312
<212> TYPE: DNA
<213> ORGANISM: H. sapiens
<220> FEATURE:
<221> NAME/KEY: exon
<222> LOCATION: (692)...(1425)

<400> SEQUENCE: 114

```
accctcctgc tcccatctgc catgatcact ggaaaaccct catttatttt ttaaagggtc    60
cagaaaatgc taatctatag agatagaaat tagattagtg gttgcctagg gtaggatgga   120
tgcaaaattt cagagtgggg ggttagaggc tattgtatag aatcttttgg agataatact   180
gattattgta gtgaaagtaa aattctgtga atatactagg aaacattgaa ctgtacacac   240
taattggtga gtcatatggt atatgaatta tgtgtcaaca aagttttaga agacattact   300
tgcaccacga tattaaaaaa tgccgtttga gttgtataat tacttcttct ctctatgtca   360
agggcaccga acaggcagga gcctctcact tgccactgtt cttaacagta ttataaaata   420
attacataag acaggttact tacatattct aggtcataaa aattattgct tgactagagt   480
aattgtaaac ataaaagaac accaaacaca ctaaaataaa tatgaggtca tcaatctttt   540
gttggtctcc ttggcatgca cctattcaga ctgttagtat tatgtattta cttcaaattt   600
tagcagttat atttaacttt gattgatttt tcctcagata taagtatgag aaatgacaga   660
aagaaacaac aactggaaaa gaagcattgc ataagaccag gatgtctctg aaatggacgt   720
cagtctttct gctgatacag ctcagttgtt actttagctc tggaagctgt ggaaaggtgc   780
tagtgtggcc cacagaatac agccattgga taaatatgaa acaatcctg aagagcttg    840
ttcagagggg tcatgaggtg actgtgttga catcttcggc ttctactctt gtcaatgcca   900
gtaaatcatc tgctattaaa ttagaagttt atcctacatc tttaactaaa aatgatttgg   960
aagattctct tctgaaaatt ctcgatagat ggatatatgg tgtttcaaaa aatacatttt  1020
ggtcatattt ttcacaatta caagaattgt gttgggaata ttatgactac agtaacaagc  1080
tctgtaaaga tgcagttttg aataagaaac ttatgatgaa actacaagag tcaaagtttg  1140
atgtcattct ggcagatgcc cttaatccct gtggtgagct actggctgaa ctatttaaca  1200
taccctttct gtacagtctt cgattctctg ttggctacac atttgagaag aatggtggag  1260
gatttctgtt ccctccttcc tatgtacctg ttgttatgtc agaattaagt gatcaaatga  1320
ttttcatgga gaggataaaa aatatgatac atatgcttta ttttgacttt tggtttcaaa  1380
tttatgatct gaagaagtgg gaccagtttt atagtgaagt tctaggtaag tcatgtgtct  1440
aactggtgct tattaagttc taactttct gtgcctttga aggtgagctt atataaatat  1500
```

```
aatgtcagaa gatagtgttt ttaagggaaa ttatgaattg caaatgtaag atgatctatc   1560
agtctcaaaa atattataga atgttgacct tatagaatca gttagaaccc tggggccatc   1620
actactacag gacacccaga gagtcataaa ccttcattgt aaagcactaa tgatttcttt   1680
aaactatcac atatcatttt gctatacatt ttttcatctt taaaaaaagt caatagatac   1740
ctcaagaaac atcttcatga aggcagacac ataaatttag tatttacaca tatttctaga   1800
aaaattatca atgcaggatt gaggaatttg tttctctttg agttcctcag tttcctcatt   1860
tagaaattaa attttgtttt tcatgtaaga aggattcctt cacagttgag taatatagtg   1920
gctctactcc agaaacagaa gcctaaaact tgagatttct aatgtttata cattccttca   1980
ataacaggtt gacaattatt tctttcaaaa actgaaatct tgttgaaagt gaacatctaa   2040
gttttaatct atattttatt aaactgcatc tctccatcaa agaaaatagg ggccaaatta   2100
agggagagca catatctcta tgtcaataaa ttctgaaaat gttttaattc tcatttgtaa   2160
atatatttat tttaaaaatc taattatatt aagatcttac gatgaaccaa gacagtagta   2220
ggtgtaaaga tttcagtgtt gagctcaaaa aactcatggt ttactttgag aaccaaggat   2280
caagggctag cttaataaac tgtagacact ag                                 2312

<210> SEQ ID NO 115
<211> LENGTH: 1021
<212> TYPE: DNA
<213> ORGANISM: H. sapiens
<220> FEATURE:
<221> NAME/KEY: exon
<222> LOCATION: (413)...(565)

<400> SEQUENCE: 115
accatgatcc aatcacctgc cactgggtcc ctccctggac acatggggat tatggggatt     60
ataattcaag atgagaggag atttgggtgg ggacagtcaa accatattag tgacttattt    120
taataattat ttatgattgt gaatatactg atgttacatt aaagatgtga tttcttctta    180
cagatctctg aatacattgc cttccttata tatacatatg agcaacatat gcaataaata    240
aaatctaaat tatgactata tataaatgta tttatatata ttttatcaat gcacagacat    300
tttatatatg tttgggtatg ttattccaag tcctttcagg aaaatacctg catattcaaa    360
taacaattct cgtgttagct acctttttgtt ttgttttgtt ttttccatc aggaagaccc    420 actacattat ttgagacaat ggggaaagct gaaatgtggc tcattcgaac ctattgggat    480
tttgaatttc ctcgcccatt cttaccaaat gttgattttg ttggaggact tcactgtaaa    540
ccagccaaac ccctgcctaa ggtaaatgta ttcttgtttc atttgtttgc ttgacatttt    600
cagaaggaat ggctggatat gtttctttca gagtgtttaa ctcagagtga ggggaatatg    660
ggaggtcaaa acaaggact tgccattaga aaatcatata tttctgtagt atcacaagta    720
tgtgaatgtt attatcatta aagaccaaag aggtttacta gggagatttt gaaaacaggg    780
ttggttaaag taaggccttc attgtgccac ccaaaagata gtatgattca tttcttcaaa    840
aaatatttgt agagtgatta atacaaacca caggtaagtg ctggattttc agagaataaa    900
ggtagcacag tttctgctcc ctcatgcctt acattgtact ttgaaagata gaataaaaac    960
aagtgaaaaa gaaaagtcta aaaagtgtta ttaaggaaag accacaatga taaagaaata   1020
t                                                                    1021

<210> SEQ ID NO 116
<211> LENGTH: 480
```

```
<212> TYPE: DNA
<213> ORGANISM: H. sapiens
<220> FEATURE:
<221> NAME/KEY: exon
<222> LOCATION: (43)...(174)

<400> SEQUENCE: 116
tgctgttgct ctttttctgat agaacaaatt ctttcttcac aggaaatgga agagtttgtg    60
cagagctctg gagaaaatgg tattgtggtg ttttctctgg ggtcgatgat cagtaacatg   120
tcagaagaaa gtgccaacat gattgcatca gcccttgccc agatcccaca aaaggttaga   180
taaagtgcct taactgtgga tggctactaa atgaatctgt taaactcttc aagagtccat   240
tacagaaatg ttctgcctga aaatttaact gctatgatag ttctaattat ctcagacatc   300
tgttcaaagc aaaaacatat atggaagatc ttaaaatcat aaagagagga gttttggttg   360
ataataacgt tggcattaat attgtgatca gaaggaaata tatttaagag gtgctagtga   420
agtttggtat tatcatggta tcgtagcatg tacatagaaa tcactaaatt ctgccctgtc   480

<210> SEQ ID NO 117
<211> LENGTH: 1602
<212> TYPE: DNA
<213> ORGANISM: H. sapiens
<220> FEATURE:
<221> NAME/KEY: exon
<222> LOCATION: (368)...(455)
<221> NAME/KEY: exon
<222> LOCATION: (1295)...(1514)

<400> SEQUENCE: 117
tgagtcaagg gctgactttg aatagaatgg gaggtaggtt tgccctaagc agcttaactt    60
ttccctttag catagagttt gggttgccaa gatttatttt cctttcacaa tctcatgtgt   120
ctagctatta tgttagaaat gtcattattt ctttatatac aaaattgatt ataaaagtaa   180
cgacattaaa cgtgggtatt caacttacct caaacttta gtagttctca ttacttgaca   240
tcacttcttc ttatttcttc atcttttata tggattaact aactgattat taatctcttc   300
agaattctaa catgctatgt ttttagagtt ctattcattg aacaagatat tttccttgcc   360
ctaacaggtt ctatggagat ttgatggcaa gaagccaaat actttaggtt ccaatactcg   420
actgtacaag tggttacccc agaatgacct tcttggtaag attctggaga acaaacagtg   480
aatatattag taacagcaaa ttggagtgat aatagttcaa cataaaacaa acatatttag   540
catttattat tggaaaacta aaaaacaaat caaatttaac tactttatat ttattttcca   600
gtcttagtat aaaaagaatg cactatagta gttggcattt tattacatac agtcacattc   660
tttatggtca gaataaaaat ctctttgttc aggtgtaatt tcctctcaca ggttttaaat   720
aacatcctgg atttttctgtc tgtctcctat ttatgcagct ttacctctgt tctttcccct   780
actgcagggt tatttcaaca ggcactgaaa atagcggaca cttttctat taccagtgac   840 tctactttt atgggaataa ataaccaatc tttatcatga taaaatgata acacatttca   900
tgatgatgca taaccggtcc ttcctcagcc ccacctccac cctactccct gctgccttt    960 aaaaaaaatt aaatatttta aatatttaa gtatttaaat atttttaaa tatgtaaatg   1020 tgacctcatt atttataata cttaaaagac cacgttcttg tatacccaat cttattcttt   1080 tttttgcac atttaattt tttaattaag aatatgcttt tcatttgt tcacctggca   1140 attcttctga aatttgaaaa caatttcaat gcagttttgt gggtataatg ttacctaggg   1200
aacagttttg ctttaagttc cttatattgt gcatttctta ttcaattctc ataccttgta   1260
```

-continued

| | |
|---|---|
| attaataatt ttgttaaaat gcatccactt ttaggtcatc ccaaaaccaa agcttttata | 1320 |
| actcatggtg gaaccaatgg catctatgag gcgatctacc atgggatccc tatggtgggc | 1380 |
| attcccttgt ttgcggatca acatgataac attgctcaca tgaaagccaa gggagcagcc | 1440 |
| ctcagtgtgg acatcaggac catgtcaagt agagatttgc tcaatgcatt gaagtcagtc | 1500 |
| attaatgacc ctgtgtgagt attacagttt tgtgaccagg tggtatttat aaattatttt | 1560 |
| gtcaacagtg aatatgaatt ttaacccgtt tttaagagac ta | 1602 |

<210> SEQ ID NO 118
<211> LENGTH: 978
<212> TYPE: DNA
<213> ORGANISM: H. sapiens
<220> FEATURE:
<221> NAME/KEY: exon
<222> LOCATION: (326)...(978)

<400> SEQUENCE: 118

| | |
|---|---|
| caaaaagatc attctcaaat tccatttcca ctatcttact tatagcactt agaatggctc | 60 |
| ataatatttt ctgctccaga aaacattaac tttcccaccg aaaattccat ttttcatttt | 120 |
| taaaggtatt tgtcagtgat aaaactccaa tttaaaaacc aaactttctg taatgacatg | 180 |
| aattaaaaca ttgaaatttc atgccaattc agtgacactt actttcaatc atttgtgtga | 240 |
| cactttcaa agaccatcca tagacttgat atgcttaagc aataaattta cttttaatgt | 300 |
| tgatatcttt atatttatcc ttcagctata aagagaatgt catgaaatta tcaagaattc | 360 |
| atcatgacca accaatgaag cccctggatc gagcagtctt ctggattgag tttgtcatgc | 420 |
| gccacaaagg agccaagcac cttcgagtcg cagctcacaa cctcacctgg atccagtacc | 480 |
| actctttgga tgtgatagca ttcctgctgg cctgcgtggc aactgtgata tttatcatca | 540 |
| caaaattttg cctgttttgt ttccgaaagc ttgccaaaac aggaaagaag aagaaaagag | 600 |
| attagttata tcaaaagcct gaagtggaat gactgaaaga tgggactcct cctttatttc | 660 |
| agcatggagg gttttaaatg gaggatttcc ttttcctgt gacaaaacat cttttcacta | 720 |
| cttaccttgt taagacaaaa tttattttcc agggatttaa tacgtacttt agttggaatt | 780 |
| attctatgtc aatgattttt aagctatgaa aaatacaatg gggggaagga tagcatttgg | 840 |
| agatatacct aatgttaaat gacgagttac tggatgcagc acgccaacat ggcacatgta | 900 |
| tacatatgta gctaacctca cgttgtgcac atgtacccta aaacttaaag tataatttaa | 960 |
| aaaaagcaaa gggtaccg | 978 |

<210> SEQ ID NO 119
<211> LENGTH: 20
<212> TYPE: DNA
<213> ORGANISM: H. sapiens

<400> SEQUENCE: 119

| | |
|---|---|
| catgcaccta ttcagactgt | 20 |

<210> SEQ ID NO 120
<211> LENGTH: 20
<212> TYPE: DNA
<213> ORGANISM: H. sapiens

<400> SEQUENCE: 120

| | |
|---|---|
| tgggtgtcct gtagtagtga | 20 |

<210> SEQ ID NO 121

```
<211> LENGTH: 25
<212> TYPE: DNA
<213> ORGANISM: H. sapiens

<400> SEQUENCE: 121
attgattttt cctcagatat aagta                                            25

<210> SEQ ID NO 122
<211> LENGTH: 22
<212> TYPE: DNA
<213> ORGANISM: H. sapiens

<400> SEQUENCE: 122
tcataatttc ccttaaaaac ac                                               22

<210> SEQ ID NO 123
<211> LENGTH: 22
<212> TYPE: DNA
<213> ORGANISM: H. sapiens

<400> SEQUENCE: 123
atatgtttgg gtatgttatt cc                                               22

<210> SEQ ID NO 124
<211> LENGTH: 18
<212> TYPE: DNA
<213> ORGANISM: H. sapiens

<400> SEQUENCE: 124
ccatattccc ctcactct                                                    18

<210> SEQ ID NO 125
<211> LENGTH: 23
<212> TYPE: DNA
<213> ORGANISM: H. sapiens

<400> SEQUENCE: 125
atacctgcat attcaaataa caa                                              23

<210> SEQ ID NO 126
<211> LENGTH: 18
<212> TYPE: DNA
<213> ORGANISM: H. sapiens

<400> SEQUENCE: 126
tatccagcca ttccttct                                                    18

<210> SEQ ID NO 127
<211> LENGTH: 22
<212> TYPE: DNA
<213> ORGANISM: H. sapiens

<400> SEQUENCE: 127
agttttgtgg gtataatgtt ac                                               22

<210> SEQ ID NO 128
<211> LENGTH: 19
<212> TYPE: DNA
<213> ORGANISM: H. sapiens

<400> SEQUENCE: 128
aaacgggtta aaattcata                                                   19
```

-continued

<210> SEQ ID NO 129
<211> LENGTH: 25
<212> TYPE: DNA
<213> ORGANISM: H. sapiens

<400> SEQUENCE: 129
tcataccttg taattaataa ttttg    25

<210> SEQ ID NO 130
<211> LENGTH: 20
<212> TYPE: DNA
<213> ORGANISM: H. sapiens

<400> SEQUENCE: 130
cgggttaaaa ttcatattca    20

<210> SEQ ID NO 131
<211> LENGTH: 18
<212> TYPE: DNA
<213> ORGANISM: H. sapiens

<400> SEQUENCE: 131
tcatgccaat tcagtgac    18

<210> SEQ ID NO 132
<211> LENGTH: 17
<212> TYPE: DNA
<213> ORGANISM: H. sapiens

<400> SEQUENCE: 132
accctccatg ctgaaat    17

<210> SEQ ID NO 133
<211> LENGTH: 21
<212> TYPE: DNA
<213> ORGANISM: H. sapiens

<400> SEQUENCE: 133
tcaaagacca tccatagact t    21

<210> SEQ ID NO 134
<211> LENGTH: 19
<212> TYPE: DNA
<213> ORGANISM: H. sapiens

<400> SEQUENCE: 134
ggagtcccat ctttcagtc    19

<210> SEQ ID NO 135
<211> LENGTH: 25
<212> TYPE: DNA
<213> ORGANISM: H. sapiens

<400> SEQUENCE: 135
attgattttt cctcagatat aagta    25

<210> SEQ ID NO 136
<211> LENGTH: 19
<212> TYPE: DNA
<213> ORGANISM: H. sapiens

<400> SEQUENCE: 136
atttactggc attgacaag    19

<210> SEQ ID NO 137
<211> LENGTH: 25
<212> TYPE: DNA
<213> ORGANISM: H. sapiens

<400> SEQUENCE: 137
attgattttt cctcagatat aagta                                   25

<210> SEQ ID NO 138
<211> LENGTH: 22
<212> TYPE: DNA
<213> ORGANISM: H. sapiens

<400> SEQUENCE: 138
tgtacagaaa gggtatgtta aa                                      22

<210> SEQ ID NO 139
<211> LENGTH: 20
<212> TYPE: DNA
<213> ORGANISM: H. sapiens

<400> SEQUENCE: 139
aaaaatkatt tggaagattc                                         20

<210> SEQ ID NO 140
<211> LENGTH: 22
<212> TYPE: DNA
<213> ORGANISM: H. sapiens

<400> SEQUENCE: 140
tcataatttc ccttaaaaac ac                                      22

<210> SEQ ID NO 141
<211> LENGTH: 23
<212> TYPE: DNA
<213> ORGANISM: H. sapiens

<400> SEQUENCE: 141
atacctgcat attcaaataa caa                                     23

<210> SEQ ID NO 142
<211> LENGTH: 18
<212> TYPE: DNA
<213> ORGANISM: H. sapiens

<400> SEQUENCE: 142
tatccagcca ttccttct                                           18

<210> SEQ ID NO 143
<211> LENGTH: 25
<212> TYPE: DNA
<213> ORGANISM: H. sapiens

<400> SEQUENCE: 143
tcataccttg taattaataa ttttg                                   25

<210> SEQ ID NO 144
<211> LENGTH: 20
<212> TYPE: DNA
<213> ORGANISM: H. sapiens

<400> SEQUENCE: 144
cgggttaaaa ttcatattca                                         20

<210> SEQ ID NO 145
<211> LENGTH: 21
<212> TYPE: DNA
<213> ORGANISM: H. sapiens

<400> SEQUENCE: 145
tcaaagacca tccatagact t                                              21

<210> SEQ ID NO 146
<211> LENGTH: 19
<212> TYPE: DNA
<213> ORGANISM: H. sapiens

<400> SEQUENCE: 146
ggagtcccat ctttcagtc                                                 19

<210> SEQ ID NO 147
<211> LENGTH: 20
<212> TYPE: DNA
<213> ORGANISM: H. sapiens

<400> SEQUENCE: 147
tgatacagct cagttgttac                                                20

<210> SEQ ID NO 148
<211> LENGTH: 20
<212> TYPE: DNA
<213> ORGANISM: H. sapiens

<400> SEQUENCE: 148
tgatacagct cggttgttac                                                20

<210> SEQ ID NO 149
<211> LENGTH: 20
<212> TYPE: DNA
<213> ORGANISM: H. sapiens

<400> SEQUENCE: 149
tgttgacatc ttcggcttct                                                20

<210> SEQ ID NO 150
<211> LENGTH: 20
<212> TYPE: DNA
<213> ORGANISM: H. sapiens

<400> SEQUENCE: 150
tgttgacatc gtcggcttct                                                20

<210> SEQ ID NO 151
<211> LENGTH: 23
<212> TYPE: DNA
<213> ORGANISM: H. sapiens

<400> SEQUENCE: 151
ctttaactaa aaatgatttg gaa                                            23

<210> SEQ ID NO 152
<211> LENGTH: 23
<212> TYPE: DNA
<213> ORGANISM: H. sapiens

<400> SEQUENCE: 152

-continued ctttaactaa aaattatttg gaa                                              23

<210> SEQ ID NO 153
<211> LENGTH: 22
<212> TYPE: DNA
<213> ORGANISM: H. sapiens

<400> SEQUENCE: 153
tttaacatac cctttctgta ca                                               22

<210> SEQ ID NO 154
<211> LENGTH: 22
<212> TYPE: DNA
<213> ORGANISM: H. sapiens

<400> SEQUENCE: 154
tttaacatac cctttccgta ca                                               22

<210> SEQ ID NO 155
<211> LENGTH: 22
<212> TYPE: DNA
<213> ORGANISM: H. sapiens

<400> SEQUENCE: 155
ttggaggact tcactgtaaa cc                                               22

<210> SEQ ID NO 156
<211> LENGTH: 22
<212> TYPE: DNA
<213> ORGANISM: H. sapiens

<400> SEQUENCE: 156
ttggaggact tcagtgtaaa cc                                               22

<210> SEQ ID NO 157
<211> LENGTH: 23
<212> TYPE: DNA
<213> ORGANISM: H. sapiens

<400> SEQUENCE: 157
tatgaggcga tctaccatgg gat                                              23

<210> SEQ ID NO 158
<211> LENGTH: 23
<212> TYPE: DNA
<213> ORGANISM: H. sapiens

<400> SEQUENCE: 158
tatgaggcaa tctaccatgg gat                                              23

<210> SEQ ID NO 159
<211> LENGTH: 24
<212> TYPE: DNA
<213> ORGANISM: H. sapiens

<400> SEQUENCE: 159
cccttgtttg cggatcaaca tgat                                             24

<210> SEQ ID NO 160
<211> LENGTH: 24
<212> TYPE: DNA
<213> ORGANISM: H. sapiens

<400> SEQUENCE: 160

```
                                                    -continued ccctttgtttg tggatcaaca tgat                                                     24

<210> SEQ ID NO 161
<211> LENGTH: 22
<212> TYPE: DNA
<213> ORGANISM: H. sapiens

<400> SEQUENCE: 161
aaagagaatg tcatgaaatt at                                                        22

<210> SEQ ID NO 162
<211> LENGTH: 22
<212> TYPE: DNA
<213> ORGANISM: H. sapiens

<400> SEQUENCE: 162
aaagagaata tcatgaaatt at                                                        22

<210> SEQ ID NO 163
<211> LENGTH: 21
<212> TYPE: DNA
<213> ORGANISM: H. sapiens

<400> SEQUENCE: 163
gcttgccaaa acaggaaaga a                                                         21

<210> SEQ ID NO 164
<211> LENGTH: 21
<212> TYPE: DNA
<213> ORGANISM: H. sapiens

<400> SEQUENCE: 164
gcttgccaaa aaaggaaaga a                                                         21
```

GENOTYPING THE HUMAN UDP-GLUCURONOSYLTRANSFERASE 2B7 (UGT2B7) GENE

This application claims the benefit of provisional application No. 60/094,391 filed Jul. 28, 1998.

INTRODUCTION

The metabolic processes commonly involved in the biotransformation of xenobiotics have been classified into functionalization reactions (phase I reactions), in which lipophilic compounds are modified via monooxygenation, dealkylation, reduction, aromatization, or hydrolysis. These modified molecules can then be substrates for the phase II reactions, often called conjugation reactions, as they conjugate a functional group with a polar, endogenous compound. Drug glucuronidation, a major phase II conjugation reaction in the mammalian detoxification system, is catalyzed by the UDP-glucuronosyltransferases (UGTs) (Batt AM, et al. (1994) *Clin Chim Acta* 226:171–190; Burchell et al. (1995) *Life Sci.* 57:1819–31).

The UGTs are a family of enzymes that catalyze the glucuronic acid conjugation of a wide range of endogenous and exogenous substrates including phenols, alcohols, amines and fatty acids. The reactions catalyzed by UGTs permit the conversion of a large range of toxic endogenous/xenobiotic compounds to more water-soluble forms for subsequent excretion (Parkinson A (1996) *Toxicol Pathol* 24:48–57).

The UGT isoenzymes are located primarily in hepatic endoplasmic reticulum and nuclear envelope (Parkinson A (1996) *Toxicol Pathol* 24:48–57), though they are also expressed in other tissues such as kidney and skin. UGTs are encoded by a large multigene superfamily that has evolved to produce catalysts with differing but overlapping substrate specificities. Three families, UGT1, UGT2, and UGT8, have been identified within the superfamily. UGTs are assigned to one the subfamilies based on amino acid sequence identity, e.g., UGT1 family members have greater than 45% amino acid sequence identity (Mackenzie et al. (1997) *Pharmacogenetics* 7:255–69).

A single gene encodes several human UGT1 isoforms, the substrate specificity of each of which is thought to arise from differential splicing of a number of substrate-specific 5-prime regions of a single mRNA transcript to a shared 3-prime portion. On the other hand, members of the mammalian UGT2 gene subfamily, which encode the odorant and steroid-metabolizing isoforms, show nucleotide differences in sequence throughout the length of the cDNAs. This suggested that the UGT2 isoenzymes are encoded by several independent genes. The UGT2 genes have been further divided on the basis of their tissue-specific expression patterns into the UGT2A gene subfamily, which encodes olfactory-specific isoforms, and the UGT2B gene subfamily, which encodes steroid-metabolizing isoforms in the liver. Monaghan et al. (1994) *Genomics* 23:496–499 mapped the UGT2B9 and the UGT2B15 genes to chromosome 4q13, giving a provisional ordering of the genes as UGT2B9-UGT2B4-UGT2B15. The UGT2B subfamily contains phenobarbital-inducible genes, as well as numerous genes that are constitutively expressed and are involved in the glucuronidation of endogenous steroids and biogenic amines (Mackenzie, et al. supra.) Evidence suggests that UGT2B4 is exclusively expressed in human liver, and not in human kidney. Levesque et al. (1997) *Pharmacogenetics* 7:317; and Coffman et al. (1997) *Drug Metabol. and Dispos.* 25:1–4, describe UGT2B gene polymorphisms.

Alteration of the expression or function of UGTs may affect drug metabolism. For example, there may be common polymorphisms in the human UGT2B gene that alter expression or function of the protein product and cause drug exposure-related phenotypes. Thus, there is a need in the field to identify UGT2B polymorphisms in order to provide a better understanding of drug metabolism and the diagnosis of drug exposure-related phenotypes.

SUMMARY OF THE INVENTION

Genetic sequence polymorphisms are identified in the UGT2B4, UGT2B7 and UGT2B15 genes, herein generically referred to as "UGT2B genes". Nucleic acids comprising the polymorphic sequences are used in screening assays, and for genotyping individuals. The genotyping information is used to predict an individuals' rate of metabolism for UGT2B substrates, potential drug-drug interactions, and adverse/side effects. Specific polynucleotides include the polymorphic UGT2B4 sequences set forth in SEQ ID NOs:25–38; the polymorphic UGT2B7 sequences set forth in SEQ ID NOs:84–111; and the polymorphic UGT2B15 sequences set forth in SEQ ID NOs:147–164.

The nucleic acid sequences of the invention may be provided as probes for detection of UGT2B locus polymorphisms, where the probe comprises a polymorphic sequence of SEQ ID NOs:25–38; 84–111 and 147–164. The sequences may further be utilized as an array of oligonucleotides comprising two or more probes for detection of UGT2B locus polymorphisms.

Another aspect of the invention provides a method for detecting in an individual a polymorphism in UGT2B metabolism of a substrate, where the method comprises analyzing the genome of the individual for the presence of at least one UGT2B polymorphism; wherein the presence of the predisposing polymorphism is indicative of an alteration in UGT2B expression or activity. The analyzing step of the method may be accomplished by detection of specific binding between the individual's genomic DNA with an array of oligonucleotides comprising UGT2B locus polymorphic sequences. In other embodiments, the alteration in UGT2B expression or activity is tissue specific, or is in response to a UGT2B modifier that induces or inhibits UGT2B expression.

BRIEF DESCRIPTION OF THE SEQUENCE LISTING

UGT2B Reference Sequences. SEQ ID NOs: 1–6 list the sequence of the reference UGT2B4 exons, where exon 1 is SEQ ID NO:1, exon 2 is SEQ ID NO:2 and so forth. Partial sequence of the flanking introns is included; the boundaries are annotated in the SEQLIST. The cDNA sequence is set forth in SEQ ID NO:7, and the encoded amino acid sequence in SEQ ID NO:8.

SEQ ID NO:39 lists the sequence of the UGT2B7 cDNA sequence, the encoded polypeptide is provided in SEQ ID NO:40. SEQ ID NOs: 41–45 list the sequence of the reference UGT2B7 exons, where exon 1 is SEQ ID NO:41, exon 2 is SEQ ID NO:42 and so forth. Partial sequence of the flanking introns is included; the boundaries are annotated in the SEQLIST.

SEQ ID NO:112 lists the sequence of the UGT2B15 cDNA sequence, the encoded polypeptide is provided in SEQ ID NO:113. SEQ ID NOs:114–118 list the sequence of the reference UGT2B15 exons, where exon 1 is SEQ ID NO:1 14, exon 2 is SEQ ID NO:115 and so forth. Partial sequence of the flanking introns is included; the boundaries are annotated in the SEQLIST.

Primers. The PCR primers for amplification of polymorphic sequences are set forth as SEQ ID NOs:9–14; 46–66; and 135–146. The primers used in sequencing isolated polymorphic sequences are presented as SEQ ID NOs: 15–24; 67–83; and 119–134.

Polymorphisms. Polymorphic sequences of UGT2B4 are presented as SEQ ID NOs:25–38. Polymorphic sequences of UGT2B7 are presented as SEQ ID NOs:84–111. Polymorphic sequences of UGT2B15 are presented as SEQ ID NO:147–164.

DESCRIPTION OF THE SPECIFIC EMBODIMENTS

Pharmacogenetics is the association between an individual's genotype and that individual's ability to metabolize or react to a therapeutic agent. Differences in metabolism or target sensitivity can lead to severe toxicity or therapeutic failure by altering the relation between bioactive dose and blood concentration of the drug. Relationships between polymorphisms in metabolic enzymes or drug targets and both response and toxicity can be used to optimize therapeutic dose administration.

Genetic polymorphisms are identified in the UGT2B4, UGT2B7 and UGT2B15 genes. Nucleic acids comprising the polymorphic sequences are used to screen patients for altered metabolism for UGT2B substrates, potential drug-drug interactions, and adverse/side effects, as well as diseases that result from environmental or occupational exposure to toxins. The nucleic acids are used to establish animal, cell culture and in vitro cell-free models for drug metabolism.

DEFINITIONS

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a construct" includes a plurality of such constructs and reference to "the UGT2B nucleic acid" includes reference to one or more nucleic acids and equivalents thereof known to those skilled in the art, and so forth. All technical and scientific terms used herein have the same meaning as commonly understood to one of ordinary skill in the art to which this invention belongs unless clearly indicated otherwise.

UGT2B4 reference sequence. The sequence of human UGT2B4 cDNA may be accessed through Genbank, accession number Y00317, and is provided in SEQ ID NOs:1–7. The amino acid sequence of UGT2B4 is listed as SEQ ID NO:8. The sequence of human UGT2B7 may be accessed through Genbank, accession number 600068, and in the SEQLIST as described above. The sequence of human UGT2B15 may be accessed through Genbak, accession number 600069, and in the SEQLIST as described above. The nucleotide sequences provided herein differ from the published sequence at certain positions throughout the sequence. Where there is a discrepancy the provided sequence is used as a reference.

The term "wild-type" may be used to refer to the reference coding sequences of UGT2B4, UGT2B7 and UGT2B15, and the term "variant", or "UGT2B" to refer to the provided variations in the UGT2B sequences. The UGT2B4, UGT2B7 and UGT2B15 sequences are generically referred to as "UGT2B", and may be further distinguished by the species, e.g. human, mouse, etc., or by the specific gene number, e.g. UGT2B4, UGT2B7, etc. Where there is no published form, such as in the intron sequences, the term wild-type may be used to refer to the most commonly found allele. It will be understood by one of skill in the art that the designation as "wild-type" is merely a convenient label for a common allele, and should not be construed as conferring any particular property on that form of the sequence.

UGT2B polymorphic sequences. It has been found that specific sites in the UGT2B4, UGT2B7 and UGT2B15 genes sequence are polymorphic, i.e. within a population, more than one nucleotide (G, A, T, C) is found at a specific position. Polymorphisms may provide functional differences in the genetic sequence, through changes in the encoded polypeptide, changes in mRNA stability, binding of transcriptional and translation factors to the DNA or RNA, and the like. The polymorphisms are also used as single nucleotide polymorphisms (SNPs) to detect genetic linkage to phenotypic variation in activity and expression of the particular UGT2B protein.

SNPs are generally biallelic systems, that is, there are two alleles that an individual may have for any particular marker. SNPs, found approximately every kilobase, offer the potential for generating very high density genetic maps, which will be extremely useful for developing haplotyping systems for genes or regions of interest, and because of the nature of SNPs, they may in fact be the polymorphisms associated with the disease phenotypes under study. The low mutation rate of SNPs also makes them excellent markers for studying complex genetic traits.

SNPs are provided in the UGT2B4, UGT2B7 and UGT2B15 intron and exon sequences. Tables 4, 7 and 10, and the corresponding sequence listing, provide both forms of each polymorphic sequence. For example, SEQ ID NO:37 and 38 are the alternative forms of a single polymorphic site. The provided sequences also encompass the complementary sequence corresponding to any of the provided polymorphisms.

In order to provide an unambiguous identification of the specific site of a polymorphism, sequences flanking the polymorphic site are shown in the tables, where the 5' and 3' flanking sequence is non-polymorphic, and the central position, shown in bold, is variable. It will be understood that there is no special significance to the length of non-polymorphic flanking sequence that is included, except to aid in positioning the polymorphism in the genomic sequence. The UGT2B exon sequences have been published, and therefore one of each pair of the sequences from exons in Tables 4, 7 and 10 are publically known sequence. The intron sequence has not been published, and hence both forms of this polymorphic sequence is novel.

As used herein, the term "UGT2B4, UGT2B7 and UGT2B15 genes" is intended to generically refer to both the wild-type and variant forms of the sequence, unless specifically denoted otherwise. As it is commonly used in the art, the term "gene" is intended to refer to the genomic region encompassing the 5' UTR, exons, introns, and the 3' UTR. Individual segments may be specifically referred to, e.g. exon 2, intron 5, etc. Combinations of such segments that provide for a complete UGT2B protein may be referred to generically as a protein coding sequence.

Nucleic acids of interest comprise the provided UGT2B nucleic acid sequence(s), as set forth in Tables 4, 7 and 10.

Such nucleic acids include short hybridization probes, protein coding sequences, variant forms of UGT2B cDNA, segments, e.g. exons, introns, etc., and the like. Methods of producing nucleic acids are well-known in the art, including chemical synthesis, cDNA or genomic cloning, PCR amplification, etc.

For the most part, DNA fragments will be of at least 15 nt, usually at least 20 nt, often at least 50 nt. Such small DNA fragments are useful as primers for PCR, hybridization screening, etc. Larger DNA fragments, i.e. greater than 100 nt are useful for production of the encoded polypeptide, promoter motifs, etc. For use in amplification reactions, such as PCR, a pair of primers will be used. The exact composition of primer sequences is not critical to the invention, but for most applications the primers will hybridize to the subject sequence under stringent conditions, as known in the art.

The UGT2B nucleic acid sequences are isolated and obtained in substantial purity, generally as other than an intact or naturally occurring mammalian chromosome. Usually, the DNA will be obtained substantially free of other nucleic acid sequences that do not include a UGT2B sequence or fragment thereof, generally being at least about 50%, usually at least about 90% pure and are typically "recombinant", i.e. flanked by one or more nucleotides with which it is not normally associated on a naturally occurring chromosome.

For screening purposes, hybridization probes of the polymorphic sequences may be used where both forms are present, either in separate reactions, spatially separated on a solid phase matrix, or labeled such that they can be distinguished from each other. Assays may utilize nucleic acids that hybridize to one or more of the described polymorphisms.

An array may include all or a subset of the polymorphisms listed in Tables 4, 7 and 10. One or both polymorphic forms may be present in the array, for example the polymorphism of SEQ ID NOS:37 and 38 may be represented by either, or both, of the listed sequences. Usually such an array will include at least 2 different polymorphic sequences, i.e. polymorphisms located at unique positions within the locus, and may include all of the provided polymorphisms. Arrays of interest may further comprise sequences, including polymorphisms, of other genetic sequences, particularly other sequences of interest for pharmacogenetic screening, e.g. UGT1, other UGT2 sequences, cytochrome oxidase polymorphisms, etc. The oligonucleotide sequence on the array will usually be at least about 12 nt in length, may be the length of the provided polymorphic sequences, or may extend into the flanking regions to generate fragments of 100 to 200 nt in length. For examples of arrays, see Ramsay (1998) *Nat. Biotech.* 16:4044; Hacia et al. (1996) *Nature Genetics* 14:441–447; Lockhart et al. (1 996) *Nature Biotechnol.* 14:1675–1680; and De Risi et al. (1996) *Nature Genetics* 14:457–460.

Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates,where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2–5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The a-anomer of deoxyribose may be used, where the base is inverted with respect to the natural b-anomer. The 2'-OH of the ribose sugar may be altered to form 2'-O-methyl or 2'-O-allyl sugars, which provides resistance to degradation without compromising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

UGT2B polypeptides. A subset of the provided nucleic acid polymorphisms in UGT2B exons confer a change in the corresponding amino acid sequence. Using the amino acid sequence provided in SEQ ID NO:8 as a reference for UGT2B4, the amino acid polymorphisms of the invention include lys→asn, pos. 40; and glu→asp, pos. 454. Using the amino acid sequence provided in SEQ ID NO:40 as a reference for UGT2B7, the amino acid polymorphisms of the invention include leu→phe, pos. 107; thr→ile, pos. 179; and lys→gln, pos. 430. Using the amino acid sequence provided in SEQ ID NO:125 as a reference for UGT2B15, the amino acid polymorphisms of the invention include ser→gly, pos. 15; asp→tyr, pos. 85; leu→pro, pos. 170; his→gln, pos. 282; ala→val, pos. 398; val→ile, pos. 443; and thr→lys, pos. 523.

Polypeptides comprising at least one of the provided polymorphisms (UGT2B$^v$ polypeptides) are of interest. The term "UGT2B$^v$ polypeptides" as used herein includes complete UGT2B protein forms, e.g. such splicing variants as known in the art, and fragments thereof, which fragments may comprise short polypeptides, epitopes, functional domains; binding sites; etc.; and including fusions of the subject polypeptides to other proteins or parts thereof. Polypeptides will usually be at least about 8 amino acids in length, more usually at least about 12 amino acids in length, and may be 20 amino acids or longer, up to substantially the complete protein.

The UGT2B4, UGT2B7 and UGT2B15 genetic sequences, including polymorphisms, may be employed for polypeptide synthesis. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host. The polypeptides may be expressed in prokaryotes or eukaryotes in accordance with conventional ways, depending upon the purpose for expression. Small peptides can also prepared by chemical synthesis.

Substrate. A substrate is a chemical entity that is modified by UGT2B4, UGT2B7 or UGT2B15, usually under normal physiological conditions. Although the duration of drug action tends to be shortened by metabolic transformation, drug metabolism is not "detoxification". Frequently the metabolic product has greater biologic activity than the drug itself. In some cases the desirable pharmacologic actions are entirely attributable to metabolites, the administered drugs themselves being inert. Likewise, the toxic side effects of some drugs may be due in whole or in part to metabolic products.

Substrates can be either endogenous substrates, i.e. substrates normally found within the natural environment of UGT2B, such as estriol, or exogenous, i.e. substrates that are not normally found within the natural environment of UGT2B. UGT2B catalyzes glucuronidation of its substrates. The enzymes are specific for UDP-glucuronic acid, and not other UDP sugars.

Exemplary UGT2B4 substrates (i.e., substrates of wild-type UGT2B4 and/or UGT2B4$^v$ polypeptides) include, but are not necessarily limited to estriol and the catechol estrogens 4-hydroxyestrone, and 2-hydroxyestriol, 2-aminophenol, 4-methylumbellifereone, 1-naphthol, 4-hydroxybiphenyl and 4-nitrophenol, 2-aminophenol, 4-hydroxybiphenyl, menthol, etc., among other substrates (Burchell et al. (1991) *DNA Cell Biol* 10:487–494, Jin C J, et al. (1993) *Biochem Biophys Res Commun* 194:496–503).

Exemplary UGT2B7 substrates (i.e., substrates of wild-type UGT2B7 and/or UGT2B7$^v$ polypeptides) include, but are not necessarily limited to oxazepam, hyodeoxycholic acid, estriol, S-naproxen, ketoprofen, ibuprofen, fenoprofen, clofibric acid (Patel et al (1995) Pharmacogenetics 5(1) :43–49), morphine (Coffman et al (1997) *Drug Metabolism and Disposition* 25:1–4), DMXAA (5,6-dimethylxantheonone4-acetic acid) (Miners et al (1997) Cancer Res 57:284), 2-Hydroxy AAF, 4 methylumbelliferone, carboxylic acid drugs (BP-7,8-trans diol) (Burchell et al., supra.)

Exemplary UGT2B15 substrates (Le., substrates of wild-type UGT2B15 and/or UGT2B15$^v$ polypeptides) include, but are not necessarily limited to 4-hydroxybiphenyl, 1-naphthol,4 methylumbelliferone, naringenin, eugenol (Burchell et al., supra.), simple phenolic compounds, 7-hydroxylated coumarins, flavonoids, anthraquinones; endogenous estrogens and androgens (Green et al. (1994) *Drug Metabolism and Disposition* 22:799.

Modifier. A modifier is a chemical agent that modulates the action of a UGT2B molecule, either through altering its enzymatic activity (enzymatic modifier) or through modulation of expression (expression modifier, e.g., by affecting transcription or translation). In some cases the modifier may also be a substrate.

Pharmacokinetic parameters. Pharmacokinetic parameters provide fundamental data for designing safe and effective dosage regimens. A drug's volume of distribution, clearance, and the derived parameter, half-life, are particularly important, as they determine the degree of fluctuation between a maximum and minimum plasma concentration during a dosage interval, the magnitude of steady state concentration and the time to reach steady state plasma concentration upon chronic dosing. Parameters derived from in vivo drug administration are useful in determining the clinical effect of a particular UGT2B genotype.

Expression assay. An assay to determine the effect of a sequence polymorphism on UGT2B expression. Expression assays may be performed in cell-free extracts, or by transforming cells with a suitable vector. Alterations in expression may occur in the basal level that is expressed in one or more cell types, or in the effect that an expression modifier has on the ability of the gene to be inhibited or induced. Expression levels of a variant alleles are compared by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

Gel shift or electrophoretic mobility shift assay provides a simple and rapid method for detecting DNA-binding proteins (Ausubel, F. M. et al. (1989) In: Current Protocols in Molecular Biology, Vol. 2, John Wiley and Sons, New York). This method has been used widely in the study of sequence-specific DNA-binding proteins, such as transcription factors. The assay is based on the observation that complexes of protein and DNA migrate through a nondenaturing polyacrylamide gel more slowly than free DNA fragments or double-stranded oligonucleotides. The gel shift assay is performed by incubating a purified protein, or a complex mixture of proteins (such as nuclear or cell extract preparations), with an end-labeled DNA fragment containing the putative protein binding site. The reaction products are then analyzed on a nondenaturing polyacrylamide gel. The specificity of the DNA-binding protein for the putative binding site is established by competition experiments using DNA fragments or oligonudeotides containing a binding site for the protein of interest, or other unrelated DNA sequences.

Expression assays can be used to detect differences in expression of polymorphisms with respect to tissue specificity, expression level, or expression in response to exposure to various substrates, and/or timing of expression during development. For example, since UGT2B4 is expressed in liver, polymorphisms could be evaluated for expression in tissues other than liver, or expression in liver tissue relative to a reference UGT2B4 polypeptide.

Substrate screening assay. Substrate screening assays are used to determine the metabolic activity of a UGT2B protein or peptide fragment on a substrate. Many suitable assays are known in the art, including the use of primary or cultured cells, genetically modified cells (e.g., where DNA encoding the UGT2B polymorphism to be studied is introduced into the cell within an artificial construct), cell-free systems, e.g. microsomal preparations or recombinantly produced enzymes in a suitable buffer, or in animals, including human clinical trials (see, e.g., Burchell et al. (1995) *Life Sci.* 57:1819–1831, specifically incorporated herein by reference. Where genetically modified cells are used, since most cell lines do not express UGT2B activity (liver cells lines being the exception), introduction of artificial construct for expression of the UGT2B polymorphism into many human and non-human cell lines does not require additional modification of the host to inactivate endogenous UGT2B expression/activity. Clinical trials may monitor serum, urine, etc. levels of the substrate or its metabolite(s).

Typically a candidate substrate is input into the assay system, and the conversion to a metabolite is measured over time. The choice of detection system is determined by the substrate and the specific assay parameters. Assays are conventionally run, and will include negative and positive controls, varying concentrations of substrate and enzyme, etc.

Genotyping: UGT2B genotyping is performed by DNA or RNA sequence and/or hybridization analysis of any convenient sample from a patient, e.g. biopsy material, blood sample (serum, plasma, etc.), buccal cell sample, etc. A nucleic acid sample from an individual is analyzed for the presence of polymorphisms in UGT2B, particularly those that affect the activity or expression of UGT2B. Specific sequences of interest include any polymorphism that leads to changes in basal expression in one or more tissues, to changes in the modulation of UGT2B expression by modifiers, or alterations in UGT2B substrate specificity and/or activity.

Linkage Analysis: Diagnostic screening may be performed for polymorphisms that are genetically linked to a phenotypic variant in UGT2B activity or expression, particularly through the use of microsatellite markers or SNPs. The microsatellite marker or SNP itself may not phenotypically expressed, but is linked to sequences that result in altered activity or expression. Two polymorphic variants may be in linkage disequilibrium, i.e. where alleles show non-random associations between genes even though individual loci are in Hardy-Weinberg equilibrium.

Linkage analysis may be performed alone, or in combination with direct detection of phenotypically evident polymorphisms. The use of microsatellite markers for genotyping is well documented. For examples, see Mansfield et al. (1994) *Genomics* 24:225–233; and Ziegle et al. (1992) *Genomics* 14:1026–1031. The use of SNPs for genotyping is illustrated in Underhill et al. (1996) *Proc Natl Acad Sci USA* 93:196–200.

Transgenic animals. The subject nucleic acids can be used to generate genetically modified non-human animals or site specific gene modifications in cell lines. The term "transgenic" is intended to encompass genetically modified animals having a deletion or other knock-out of UGT2B4, UGT2B7 or UGT2B15 activity, having an exogenous UGT2B4, UGT2B7 or UGT2B15 gene that is stably transmitted in the host cells, or having an exogenous UGT2B promoter operably linked to a reporter gene. Transgenic animals may be made through homologous recombination, where the UGT2B locus is altered. Alternatively, a nucleic acid construct is randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

Genetically Modified Cells. Primary or cloned cells and cell lines are modified by the introduction of vectors comprising UGT2B4, UGT2B7 and UGT2B15 genetic polymorphisms. The gene may comprise one or more variant sequences, preferably a haplotype of commonly occurring combinations. In one embodiment of the invention, a panel of two or more genetically modified cell lines, each cell line comprising a UGT2B polymorphism, are provided for substrate and/or expression assays. The panel may further comprise cells genetically modified with other genetic sequences, including polymorphisms, particularly other sequences of interest for pharmacogenetic screening, e.g. UGT1, other UGT2 sequences, cytochrome oxidase polymorphisms, etc.

Vectors useful for introduction of the gene include plasmids and viral vectors, e.g. retroviral-based vectors, adenovirus vectors, etc. that are maintained transiently or stably in mammalian cells. A wide variety of vectors can be employed for transfection and/or integration of the gene into the genome of the cells. Alternatively, micro-injection may be employed, fusion, or the like for introduction of genes into a suitable host cell.

GENOTYPING METHODS

The effect of a polymorphism in the UGT2B4, UGT2B7 or UGT2B15 gene sequence on the response to a particular substrate or modifier is determined by in vitro or in vivo assays. Such assays may include monitoring the metabolism of a substrate during clinical trials to determine the UGT2B enzymatic activity, specificity or expression level. Generally, in vitro assays are useful in determining the direct effect of a particular polymorphism, while clinical studies will also detect an enzyme phenotype that is genetically linked to a polymorphism.

The response of an individual to the substrate or modifier can then be predicted by determining the UGT2B genotype, with respect to the polymorphism. Where there is a differential distribution of a polymorphism by racial background, guidelines for drug administration can be generally tailored to a particular ethnic group.

The basal expression level in different tissue may be determined by analysis of tissue samples from individuals typed for the presence or absence of a specific polymorphism. Any convenient method may be used, e.g. ELISA, RIA, etc. for protein quantitation, northern blot or other hybridization analysis, quantitative RT-PCR, etc. for mRNA quantitation. The tissue specific expression is correlated with the genotype.

The alteration of UGT2B expression in response to a modifier is determined by administering or combining the candidate modifier with an expression system, e.g. animal, cell, in vitro transcription assay, etc. The effect of the modifier on UGT2B transcription and/or steady state mRNA levels is determined. As with the basal expression levels, tissue specific interactions are of interest. Correlations are made between the ability of an expression modifier to affect UGT2B activity, and the presence of the provided polymorphisms. A panel of different modifiers, cell types, etc. may be screened in order to determine the effect under a number of different conditions.

A UGT2B polymorphism that results in altered enzyme activity or specificity is determined by a variety of assays known in the art. The enzyme may be tested for metabolism of a substrate in vitro, for example in defined buffer, or in cell or subcellular lysates, where the ability of a substrate to be metabolized by UGT2B4, UGT2B7 or UGT2B15 under physiologic conditions is determined. Where there are not significant issues of toxicity from the substrate or metabolite (s), in vivo human trials may be utilized, as previously described.

The genotype of an individual is determined with respect to the provided UGT2B4, UGT2B7 and UGT2B15 polymorphisms. The genotype is useful for determining the presence of a phenotypically evident polymorphism, and for determining the linkage of a polymorphism to phenotypic change.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. The nucleic acid may be amplified by conventional techniques, such as the polymerase chain reaction (PCR), to provide sufficient amounts for analysis. The use of the polymerase chain reaction is described in Saiki et al. (1985) *Science* 230:1350–1354, and a review of current techniques may be found in Sambrook et al *Molecular Cloning: A Laboratory Manual*, CSH Press 1989, pp.14.2–14.33. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al (1990) *Nucleic Acids Res* 18:2887–2890; and Delahunty et al (1996) *Am J Hum Genet* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), mismatch cleavage detection, and heteroduplex analysis in gel matrices are used to detect conformational changes created by DNA sequence variation as alterations in electrophoretic mobility. Alternatively, where a polymorphism creates or destroys a recognition site for a restriction endonuclease (restriction fragment length polymorphism, RFLP), the sample is digested with that endonuclease, and the products size fractionated to determine whether the fragment was digested. Fractionation is performed by gel or capillary electrophoresis, particularly acrylamide or agarose gels.

In one embodiment of the invention, an array of oligonucleotides are provided, where discrete positions on the array are complementary to one or more of the provided polymorphic sequences, e.g. oligonucleotides of at least 12 nt, frequently 20 nt, or larger, and including the sequence flanking the polymorphic position. Such an array may comprise a series of oligonucleotides, each of which can specifically hybridize to a different polymorphism. For examples of arrays, see Hacia et al. (1996) *Nat Genet* 14:441–447 and DeRisi et al. (1996) *Nat Genet* 14:457–460.

The genotype information is used to predict the response of the individual to a particular UGT2B substrate or modifier. Where an expression modifier inhibits UGT2B expression, then drugs that are a UGT2B substrate will be metabolized more slowly if the modifier is co-administered. Where an expression modifier induces UGT2B expression, a co-administered substrate will typically be metabolized more rapidly. Similarly, changes in UGT2B activity will affect the metabolism of an administered drug. The pharmacokinetic effect of the interaction will depend on the metabolite that is produced, e.g. a prodrug is metabolized to an active form, a drug is metabolized to an inactive form, an environmental compound is metabolized to a toxin, etc. Consideration is given to the route of administration, drug-drug interactions, drug dosage, etc.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g., amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Genotyping UGT2B4

Materials and Methods

DNA Samples. Blood specimens from approximately 48 individuals were collected after obtaining informed consent. All samples were stripped of personal identifiers to maintain confidentiality. The only data associated with a given blood samples was gender and self-reported major racial group designations in the United States (Caucasian, Hispanic, African American). Genomic DNA was isolated from these samples using standard techniques. DNA was stored either as a concentrated solution, or in a dried form in microtiter plates.

PCR amplifications. The primers used to amplify exons in which polymorphisms were found are shown in Table 1, and were designed with NBI's Oligo version 5.1 program. Sequences for exons in which no polymorphisms were found are not shown.

TABLE 1

UGT2B4 PCR Primers.
Primary PCR Amplification

| Region | Forward/Reverse | SEQ ID NO | Sequence |
|---|---|---|---|
| UGT2B4 Exon 1 | F | 9. | tacctttagttgtctctttgtca |
|  | R | 10. | ttcctggagtcttctgtatga |
| UGT2B4 Exon 4 | F | 11. | catcccttgttcttctcatt |
|  | R | 12. | cgggactggaaaataaatat |
| UGT2B4 Exon 6 | F | 13. | ggggtttcaccgtgtta |
|  | R | 14. | aaagccaagcagcactaa |

Twenty-five nanograms of gDNA were amplified in the primary amplifications using the Perkin Elmer GeneAmp PCR kit according to the manufacturer's instructions in 25 μl reactions with AmpliTaq Gold DNA polymerase. Reactions contained 25 mM $MgCl_2$ and 0.2 μM of each primer. Thermal cycling was performed using a GeneAmp PCR System 9600 PCR machine (Perkin Elmer), utilizing a touch-down PCR protocol. The protocol, unless indicated otherwise in Table 2, consisted of an initial incubation of 95° C. for 10 min, followed by ten cycles of 95° C. for 20 sec, 64° C. (minus 1° C. per cycle for 20 sec, 72° C. for 2 min, six cycles of 95° C. for 20 sec, 54° C. for 20 sec, 72° C. for 2 min, and nineteen cycles of 95° C. for 20 sec, 54° C. for 20 sec, 72° C. for 2 min (plus 15 sec per cycle), and one final extension step of 72° C. for 10 min.

For the secondary PCR reactions, one microliter of each primary PCR reaction was re-amplified using the primary PCR primers. The thermal cycling profile that was used for the primary PCR for an exon was also used for the secondary PCR.

TABLE 2

Cycling Profile Modifications

| Exon | Primary PCR | Secondary PCR |
|---|---|---|
| 1 | Touch-Down PCR step: 8 cycles 64° C. (minus 1° C. per cycle), for 15 sec Total Number of cycles: 35 | same as Primary PCR |
| 4 | Touch-Down PCR step: 10 cycles 64° C. (minus 1° C. per cycle), for 15 sec Total Number of cycles: 35 | same as Primary PCR |
| 6 | Touch-Down PCR step: 7 cycles 64° C. (minus 1° C. per cycle), for 15 sec Total Number of cycles: 35 | same as Primary PCR |

DNA sequencing. PCR products from 48 individuals (approximately ⅓ African American, ⅓ Caucasian, ⅓ Hispanic) were prepared for sequencing by treating 8 μl of each PCR product with 0.15 μl of exonuclease I (1.5 U/reaction), 0.3 μl of Shrimp Alkaline Phosphatase (0.3U/reaction), q.s. to 10 μl with MilliQ water, and incubated at 37° C. for 30 min, followed by 72° C. for 15 min. Cycle sequencing was performed on the GeneAmp PCR System 9600 PCR machine (Perkin Elmer) using the ABI Prism dRhodamine Terminator Cycle Sequencing Ready Reaction Kit according to the manufacturer's directions, with the following changes: (1) 2 μl of dRhodamine terminator premix, instead of 8 μl, (2) 10% (v/v) Dimethylsulfoxide was added to each individual nucleotide. The oligonucleotide primers (unlabelled), at 3 picomoles per reaction, used for the sequencing reactions are listed in Table 3. Sequencing reactions, with a final volume of 5 μl, were subjected to 25 cycles at 96° C. for 10 sec, 50° C. for 5 sec, and 60° C. for 4 min, followed by ethanol precipitation. After decanting the ethanol, samples were evaporated to dryness using a SpeedVac for roughly 15 min and were resuspended in 2 μl of loading buffer (5:1 deionized formamide:50 mM EDTA pH 8.0), heated to 94° C. for 2 min, and were electrophoresed through 5.25% polyacrylamide/6M urea gels in an ABI Prism 377 DNA Sequencer, according to the manufacturer's instructions for sequence determination. All sequences were determined from both the 5' and 3' (sense and antisense) direction.

TABLE 3

Sequencing Primers

| P. No. | F/R | SEQ ID NO | Forward Primer |
|---|---|---|---|
| 1 | F | 15. | ccacatgctcagactgttaa |
|   | R | 16. | caaaaatacccactaccc |
| 2 | F | 17. | cccttgttcttctcattgtta |
|   | R | 18. | ttcagtaagcttgtttcatgat |
| 3,4 | F | 19. | cctgccaaattgactt |
|   | R | 20. | caggaacccagtcacatc |
| 5 | F | 21. | ggggaaaagagattaattacg |
|   | R | 22. | agccaagcagcactaatc |
| 6,7 | F | 23. | tccaattcacaggttacatg |
|   | R | 24. | agccaagcagcactaatc |

TABLE 4

Summary of UGT2B4 polymorphisms.

| Exon | Nt change | AA change | SEQ ID | Sequence |
|---|---|---|---|---|
| 1 | G 157 C | Lys 40 Asn | 25. | tggatgaatataaagacaatcctggat |
|   |   |   | 26. | tggatgaatataaacacaatcctggat |

TABLE 4-continued

Summary of UGT2B4 polymorphisms.

| Exon | Nt change | AA change | SEQ ID | Sequence |
|---|---|---|---|---|
| Int. 4 | T 61 C |   | 27. | aagtgttaatagttatcatgaaacaag |
|   |   |   | 28. | aagtgttaatagctatcatgaaacaag |
| 6 | T 1411 A | Glu 454 Asp | 29. | tgaagcccttgatcgagcagtcttct |
|   |   |   | 30. | tgaagcccttgaacgagcagtcttct |
| 6 | C 1412 A |   | 31. | tgaagcccttgatcgagcagtcttct |
|   |   |   | 32. | tgaagcccttgatagagcagtcttct |
| 6 | T 1849 C |   | 33. | gatataaagccatacgaggttatattg |
|   |   |   | 34. | gatataaagccatatgaggttatattg |
| 6 | A 1919 C |   | 35. | caggttacatgaaaaaaaatttacta |
|   |   |   | 36. | caggttacatgaaaaacaatttacta |
| 6 | A 2072 G |   | 37. | ttgttgaggaagctaataaataattaa |
|   |   |   | 38. | ttgttgaggaaactaataaataattaa |

Nucleotide variants in exons are numbered from first base in Sequence 1. Amino Acid changes are numbered beginning with the first methionine in the protein sequence provided in Sequence 1. The nucleotide variant in intron 4 is numbered from the beginning of intron 4, as provided in sequence 2.4.

Example 2

UGT2B7 Genotyping

Twenty-five nanograms of gDNA were amplified in the primary amplifications using the Perkin Elmer GeneAmp PCR kit according to the manufacturer's instructions in 25 μl reactions with AmpliTaq Gold DNA polymerase. Reactions contained 25 mM MgCl₂ and 0.2 μM of each primer. Thermal cycling was performed using a GeneAmp PCR System 9600 PCR machine (Perkin Elmer), utilizing a touch-down PCR protocol. The exons for UGT2B7 were amplified using the following cycling conditions: An initial incubation at 96° C. for 10 min., followed by. 16 cycles of 95° C. for 20 sec., 52° C. for 20 sec., 72° C. for 2 min., and nineteen cycles of 95° C. for 20 sec, 52° C. for 20 sec, 72° C. for 2 min (plus 15 sec per cycle), and one final extension step of 72° C. for 10 min.

For the secondary PCR reactions, one microliter of each primary PCR reaction was re-amplified using the primary PCR primers. The thermal cycling profile that was used for the primary PCR for an exon was also used for the secondary PCR.

The amplification primers are provided in Table 5, the sequencing primers in Table 6, and the polymorphisms in Table 7.

TABLE 5

PCR Primers for UGT2B7 Amplification

| Region | | SEQ ID NO | Primer Sequence |
|---|---|---|---|
| UGT2B7 Exon 1 | Primary F | 46. | cttggctaatttatctttgg |
|   | Primary R | 47. | cccactaccctgactttat |
|   | Secondary F | 48. | ggacataaccatgagaaatg |
|   | Secondary R | 49. | agctctgcttcaaagacac |
| UGT2B7 Exon 2 | Primary F | 50. | tgtccgtatgctactattgaa |
|   | Primary R | 51. | tgtgctaatcccttttgtaaat |
|   | Secondary F | 52. | ttttttttctattcctgtcag |
|   | Secondary R | 53. | ctttaccccacccattt |
| UGT2B7 Exon 4 | Primary F | 54. | cccttgatctcattcctact |
|   | Primary R | 55. | aactggctattctttagatgtatg |
|   | Secondary F | 56. | cattcctactctttatacagttctc |
|   | Secondary R | 57. | cccccgattcagactat |
| UGT2B7 Exon 5 | Primary F | 58. | cccttgatctcattcctact |
|   | Primary R | 59. | aactggctattctttagatgtatg |

TABLE 5-continued

PCR Primers for UGT2B7 Amplification

| Region | | SEQ ID NO | Primer Sequence |
|---|---|---|---|
| | Secondary F | 60. | tcctccgaagtctgaaac |
| | Secondary R | 61. | tataaaaaggatgaaactcacac |
| UGT2B7 Exon 6 | Primary F | 62. | caagcccccaagttatgt |
| | Primary R | 63. | cagtaggatccgcgatataa |
| | Secondary F | 64. | tctgagggttttgtctgta |
| | Secondary R | 65. | ccgcgatataagttcaacaa |

DNA sequencing. PCR products from 48 individuals were prepared for sequencing by treating 8 μL of each PCR product with 0.15 μL of exonuclease I (1.5U/reaction), 0.3 μL of Shrimp Alkaline Phosphatase (0.3U/reaction), q.s. to 10 μL with MilliQ water, and incubated at 37° C. for 30 min, followed by 72° C. for 15 min. Cycle sequencing was performed on the GeneAmp PCR System 9600 PCR machine (Perkin Elmer) using the ABI Prism dRhodamine Terminator Cycle Sequencing Ready Reaction Kit or the ABI Prism Big Dye Terminator Cycle Sequencing Ready Reaction Kit according to the manufacturer's directions, with the following changes: For the ABI Prism dRhodamine Terminator kit, (1) 2 μL of dRhodamine terminator premix, instead of 8 μL, (2) 10% (v/v) Dimethylsulfoxide was added to each individual nucleotide, (3) 5 μL total volume instead of 20 μL. For the ABI Prism Big Dye Terminator kit (1) 0.8 μL, of Big Dye terminator premix, instead of 8 μL, and (2) 15 μL total volume instead of 20 μL. The oligonucleotide primers (unlabeled), at 3 picomoles per reaction, used for the sequencing reactions are listed in Table 6. Sequencing reactions, with a final volume of 5 μL, were subjected to 25 cycles at 96° C. for 10 sec, 50° C. for 5 sec, and 60° C. for 4 min, followed by ethanol precipitation. After decanting the ethanol, samples were evaporated to dryness using a Speed-Vac for roughly 15 min and were resuspended in 2 μl of loading buffer (5:1 deionized formamide:50 mM EDTA pH 8.0), heated to 94° C. for 2 min, and were electrophoresed through 5.25% polyacrylamide/6M urea gels in an ABI Prism 377 DNA Sequencer, according to the manufacturer's instructions for sequence determination. All sequences were determined from both the 5' and 3' (sense and antisense) direction.

TABLE 6

Sequencing Primers UGT2B7

| P. No. | F/R | SEQ ID NO | Primer Sequence |
|---|---|---|---|
| 1, 2 | F | 66. | ggacataaccatgagaaatg |
| | R | 67. | ttaagagcggatgagttgt |
| 3, 4 | F | 68. | tcatcatgcaacagattaag |
| | R | 69. | cactacagggaaaaatagca |
| 5 | F | 70. | acccttttgtacagtctca |
| | R | 71. | agctctgcttcaaagacac |
| 6, 7 | F | 72. | ttgcctacattattctaaccc |
| | R | 73. | ctttaccccacccattt |
| 8, 9 | F | 74. | cattcctactctttatacagttctc |
| | R | 75. | cccccgattcagactat |
| 10 | F | 76. | cattcctactctttatacagttctc |
| | R | 77. | cccccgattcagactat |
| 11, 12 | F | 78. | tcctccgaagtctgaaac |
| | R | 79. | tataaaaggatgaaactcacac |
| 13 | F | 80. | tctgaggggttttgtctgta |
| | R | 81. | ttttttgtctcaggaagaaga |
| 14 | F | 82. | aaaaaaagaaaaaaaatcttttc |
| | R | 83. | ccgcgatataagttcaacaa |

TABLE 7

Summary of Sequence Polymorphisms UGT2B7

| N | Exon | Nt change | AA change | SEQ ID NO. | Sequence |
|---|---|---|---|---|---|
| 1 | 1 | G 13 A | | 84. | tgcattgcaccaggatgtctgt |
| | | | | 85. | tgcattgcaccaagatgtctgt |
| 2 | 1 | T 151 C | Leu 107 Phe | 86. | tcctggatgagcttattcagaga |
| | | | | 87. | tcctggatgagcctattcagaga |
| 3 | 1 | A 236 T | | 88. | cattttggttatatttttcac |
| | | | | 89. | cattttggttttattttttcac |
| 4 | 1 | A 286 G | | 90. | cataactagaagttctgtaa |
| | | | | 91. | cataactaggaagttctgtaa |
| 5 | 1 | C 450 T | Thr 179 Ile | 92. | cctggctacactttttgaaaa |
| | | | | 93. | cctggctacatttttgaaaa |
| 6 | 2 | A 14 G | | 94. | gaagacccactacattatctg |
| | | | | 95. | gaagacccactacgttatctg |
| 7 | 2 | AT 80-81 TC | | 96. | aattttcagtttccatatccactctt |
| | | | | 97. | aattttcagtttcctcatccactctt |
| 8 | 4 | C 57 G | | 98. | taggtctcaatactcggctcta |
| | | | | 99. | taggtctcaatactcggctgta |
| 9 | 4 | C 60 T | | 100. | tacaagtggataccccaga |
| | | | | 101. | tataagtggataccccaga |
| 10 | In. 4 | A 154 del | | 102. | gggagaaagaatacattataattttt |
| | | | | 103. | gggagaaagaatacttataattttt |
| 11 | 5 | C 101 T | | 104. | ttccattgtttgccgatcaac |
| | | | | 105. | ttccattgtttgctgatcaac |
| 12 | 5 | A 198 C | Lys 430 Gln | 106. | gaatgcattgaagagagtaat |
| | | | | 107. | gaatgcattgcagagagtaat |
| 13 | 6 | A 197 G | | 108. | ctggtctgtgtggcaactgtga |
| | | | | 109. | ctggtctgtgtggcgactgtga |
| 14 | 6 | C 528 A | | 110. | taagataaagccttatgag |
| | | | | 111. | taagataaagacttatgag |

Example 3

Genotyping UGT2B15

Sequencing and analysis were performed as described in Example 2. The amplification primers are provided in Table 9, the sequencing primers in Table 8, and the polymorphisms in Table 10.

TABLE 8

Sequencing Primers UGT2B15

| Region | | | SEQ ID NO | Primer Sequence |
|---|---|---|---|---|
| UGT2B15 Exon 1 | Primary F | | 119. | catgcacctattcagactgt |
| | Primary R | | 120. | tgggtgtcctgtagtagtga |
| | Secondary F | | 121. | attgattttcctcagatataagta |
| | Secondary R | | 122. | tcataattcccttaaaaacac |
| UGT2B15 Exon 2 | Primary F | | 123. | atatgtttgggtatgttattcc |
| | Primary R | | 124. | ccatattcccctcactct |
| | Secondary F | | 125. | atacctgcatattcaaataacaa |
| | Secondary R | | 126. | tatccagccattccttct |
| UGT2B15 Exon 5 | Primary F | | 127. | agttttgtgggtataatgttac |
| | Primary R | | 128. | aaacgggttaaaattcata |
| | Secondary F | | 129. | tcataccttgtaattaataattttg |
| | Secondary R | | 130. | cgggttaaaattcatattca |
| UGT2B15 Exon 6 | Primary F | | 131. | tcatgccaattcagtgac |
| | Primary R | | 132. | accctccatgctgaaat |
| | Secondary F | | 133. | tcaaagaccatccatagactt |
| | Secondary R | | 134. | ggagtcccatctttcagtc |

TABLE 9

PCR Primers UGT2B15

| P. No. | F/R | SEQ ID NO | Primer Sequence |
|---|---|---|---|
| 1,2 | F | 135. | attgattttcctcagatataagta |
|  | R | 136. | atttactggcattgacaag |
| 3 | F | 137. | attgattttcctcagatataagta |
|  | R | 138. | tgtacagaaagggtatgttaaa |
| 4 | F | 139. | aaaaat g/t atttggaagattc |
|  | R | 140. | tcataatttcccttaaaaacac |
| 5 | F | 141. | atacctgcatattcaaataacaa |
|  | R | 142. | tatccagccattccttct |
| 6,7 | F | 143. | tcataccttgtaattaataattttg |
|  | R | 144. | cgggttaaaattcatattca |
| 8,9 | F | 145. | tcaaagaccatccatagactt |
|  | R | 146. | ggagtcccatctttcagtc |

TABLE 10

Summary of Sequence Polymorphisms UGT2B15

| N | Exon | Ntd change | AA change | SEQ ID NO. | Sequence |
|---|---|---|---|---|---|
| 1 | 1 | A 53 G | Ser 15 Gly | 147. | tgatacagctcagttgttac |
|  |  |  |  | 148. | tgatacagctcggttgttac |
| 2 | 1 | T 184 G |  | 149. | tgttgacatcttcggcttct |
|  |  |  |  | 150. | tgttgacatcgtcggcttct |
| 3 | 1 | G 263 T | Asp 85 Tyr | 151. | ctttaactaaaaatgatttggaa |
|  |  |  |  | 152. | ctttaactaaaaattatttggaa |
| 4 | 1 | T 519 C | Leu 170 Pro | 153. | tttaacataccctttctgtaca |
|  |  |  |  | 154. | tttaacataccctttccgtaca |

TABLE 10-continued

Summary of Sequence Polymorphisms UGT2B15

| N | Exon | Ntd change | AA change | SEQ ID NO. | Sequence |
|---|---|---|---|---|---|
| 5 | 2 | C 122 G | His 282 Gln | 155. | ttggaggacttcactgtaaacc |
|  |  |  |  | 156. | ttggaggacttcagtgtaaacc |
| 6 | 5 | G 59 A |  | 157. | tatgaggcgatctaccatgggat |
|  |  |  |  | 158. | tatgaggcaatctaccatgggat |
| 7 | 5 | C 100 T | Ala 398 Val | 159. | cccttgtttgcggatcaacatgat |
|  |  |  |  | 160. | cccttgtttgtggatcaacatgat |
| 8 | 6 | G 14 A | Val 443 Ile | 161. | aaagagaatgtcatgaaattat |
|  |  |  |  | 162. | aaagagaatatcatgaaattat |
| 9 | 6 | C 523 A | Thr 523 Lys | 163. | gcttgccaaaacaggaaagaa |
|  |  |  |  | 164. | gcttgccaaaaaaggaaagaa |

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated UGT2B7 nucleic acid molecule wherein said nucleic acid molecule comprises a nucleic acid selected from the group consisting of:
   (i) a nucleic acid sequence comprising at least 20 contiguous nucleotides of a nucleic acid sequence selected from the group consisting of SEQ ID NO: 85, 87, 89, 91, 103, 105, 107, 109,
   (ii) a nucleic acid molecule comprising a thymine base at position 197 of SEQ ID NO: 44 and at least 20 contiguous bases of SEQ ID NO: 44 immediately adjacent to said position 197,
   (iii) a nucleic acid molecule comprising an adenine base at position 546 of SEQ ID NO: 45 and at least 20 contiguous bases of SEQ ID NO: 45 immediately adjacent to said position 546 and
   (iv) a nucleic acid sequence that is filly complementary to a nucleic acid sequence of (i)–(iii).

2. A nucleic acid probe for the detection of a UGT2B7 gene, said probe comprising at least one polynucleotide of claim 1.

3. A nucleic acid probe according to claim 2, wherein said probe is conjugated to a detectable marker.

4. An array of oligonucleotides comprising:
   two or more probes for the detection of a UGT2B7 gene, said probes comprising at least one polynucleotide of claim 1.

5. A method for detecting in an individual a UGT2B7 gene, the method comprising:

(a) obtaining a nucleic acid sample that has been isolated from an individual; and
(b) contacting said nucleic acid sample with a UGT2B7 nucleic acid probe, wherein said UGT2B7 nucleic acid probe sequence comprises a nucleic acid selected from the group consisting of:
   (i) a nucleic acid sequence comprising at least 20 contiguous nucelcotides of a nucleic acid sequence selected from the group consisting of SEQ ID NO: 85, 87, 89, 91, 103, 105, 107,109,
   (ii) a nucleic acid molecule comprising a thymine base at position 197 of SEQ ID NO: 44 and at least 20 contiguous bases of SEQ ID NO: 44 immediately adjacent to said position 197,
   (iii) a nucleic acid molecule comprising an adenine base at position 546 of SEQ ID NO: 45 and at least 20 contiguous bases of SEQ ID NO: 45 immediately adjacent to said position 546 and
   (iv) a nucleic acid sequence that is fully complementary to a nucleic acid sequence of (i)–(iii)
(c) detecting specific hybridizaton between said probe and said nucleic acid sample as indicative of the presence of a UGT2B7 gene in said nucleic acid sample.

6. A method according to claim 5, wherein said analyzing step comprises the detection of specific binding between genomic DNA of said individual with an array of oligonucleotides comprising:
   two or more probes for the detection of a UGT2B7 gene, said probes comprising at least one polynucleotide having a nucleic acid sequence as recited in claim 5.

7. An isolated UGT2B7 polynucleotide having a polymorphism, wherein said polynucleotide comprises a polynucleotide selected from the group consisting of:

(a) SEQ ID NO: 39 with the exception that an A nucleotide is substituted for a G nucleotide at position 13 of SEQ ID NO: 39, (b) SEQ ID NO: 39 with the exception that a C nucleotide is substituted for a T nucleotide at position 151 of SEQ ID NO: 39, (c) SEQ ID NO: 39 with the exception that a T nucleotide is substituted for an A nucleotide at position 335 of SEQ ID NO: 39, (d) SEQ ID NO: 39 with the exception that a G nucleotide is substituted for an A nucleotide at position 386 of SEQ ID NO: 39, (e) SEQ ID NO: 44 with the exception that an A nucleotide is deleted at position 380 of SEQ ID NO:44, (f) SEQ ID NO: 39 with the exception that a T nucleotide is substituted for a C nucleotide at position 1205 of SEQ ID NO: 39, (g) SEQ ID NO: 39 with the exception that a C nucleotide is substituted for an A nucleotide at position 1302 of SEQ ID NO: 39, (h) SEQ ID NO 39 with the exception that a G nucleotide is substituted for an A nucleotide at position 1502 of SEQ ID NO: 39, (i) SEQ ID NO: 39 with the exception that an A nucleotide is substituted for a C nucleotide at position 1852 of SEQ ID NO: 39, and;

(j) a nucleic acid sequence that is fully complementary to a nucleic acid sequence of (a), (b), (c), (d), (e), (f), (g), (h) or (i).

* * * * *